US011110171B2

(12) United States Patent
Mor et al.

(10) Patent No.: US 11,110,171 B2
(45) Date of Patent: Sep. 7, 2021

(54) PD-1 RELATED CANCER THERAPY

(71) Applicant: New York University, New York, NY (US)

(72) Inventors: Adam Mor, Cresskill, NJ (US); Ben Neel, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 16/956,451

(22) PCT Filed: Dec. 21, 2018

(86) PCT No.: PCT/US2018/067270
§ 371 (c)(1),
(2) Date: Jun. 19, 2020

(87) PCT Pub. No.: WO2019/126736
PCT Pub. Date: Jun. 27, 2019

(65) Prior Publication Data
US 2020/0330595 A1 Oct. 22, 2020

Related U.S. Application Data

(60) Provisional application No. 62/608,998, filed on Dec. 21, 2017.

(51) Int. Cl.
| | | |
|---|---|---|
| *C07K 16/28* | (2006.01) | |
| *A61K 39/395* | (2006.01) | |
| *A61P 35/00* | (2006.01) | |
| *G01N 33/574* | (2006.01) | |
| *G01N 33/68* | (2006.01) | |
| *A61K 31/343* | (2006.01) | |
| *A61K 31/404* | (2006.01) | |
| *A61K 31/4412* | (2006.01) | |
| *A61K 31/4535* | (2006.01) | |
| *A61K 31/47* | (2006.01) | |
| *A61K 31/4704* | (2006.01) | |
| *A61K 31/497* | (2006.01) | |
| *A61K 38/46* | (2006.01) | |
| *C12N 15/113* | (2010.01) | |

(52) U.S. Cl.
CPC ........ *A61K 39/3955* (2013.01); *A61K 31/343* (2013.01); *A61K 31/404* (2013.01); *A61K 31/4412* (2013.01); *A61K 31/4535* (2013.01); *A61K 31/47* (2013.01); *A61K 31/4704* (2013.01); *A61K 31/497* (2013.01); *A61K 38/465* (2013.01); *A61P 35/00* (2018.01); *C07K 16/2803* (2013.01); *C12N 15/1137* (2013.01); *G01N 33/57484* (2013.01); *G01N 33/6848* (2013.01); *G01N 2560/00* (2013.01)

(58) Field of Classification Search
None
See application file for complete search history.

(56) References Cited

U.S. PATENT DOCUMENTS

| | | | |
|---|---|---|---|
| 9,181,553 B2 * | 11/2015 | Bentires-Alj | C07K 16/40 |
| 2004/0121384 A1 * | 6/2004 | Gelb | C07K 14/705 435/6.16 |
| 2005/0159332 A1 | 7/2005 | Moretta et al. | |
| 2008/0004215 A1 * | 1/2008 | Agazie | C07K 5/06113 514/19.3 |
| 2008/0176309 A1 * | 7/2008 | Wu | C07D 209/40 435/184 |
| 2008/0194563 A1 * | 8/2008 | Hellmuth | A61P 35/04 514/236.5 |
| 2009/0042788 A1 * | 2/2009 | Agazie | C07K 5/1021 514/1.1 |
| 2012/0034186 A1 * | 2/2012 | Wu | C07D 209/40 424/85.5 |
| 2013/0028886 A1 * | 1/2013 | Aceto | C12N 9/16 424/130.1 |
| 2016/0333072 A1 | 11/2016 | Rutenberg et al. | |
| 2017/0166510 A1 * | 6/2017 | Agazie | G01N 33/5008 |
| 2019/0350885 A1 * | 11/2019 | Kelley | A61K 31/497 |

FOREIGN PATENT DOCUMENTS

| | | | |
|---|---|---|---|
| WO | 2012/018538 A2 | 2/2012 | |
| WO | 2017/156310 A1 | 9/2017 | |
| WO | WO 2018203875 | * 11/2018 | ........... A61K 31/343 |

OTHER PUBLICATIONS

Agresta 2018 Front. Immunol. 9:2809, p. 1-9.*
Bahai 2019 Int. J. Mol. Sci. 20, 4797; p. 1-18.*
Bai 2017; Oncotarget, vol. 8, (No. 66), pp. 110693-110707.*
Bloch-Queyrat 2005; J Exp Med vol. 202, No. 1, Jul. 4, 181-192.*
Cai 2019 OncoTargets and Therapy 12: 8437-8445.*
Cannons 2011 Annu. Rev. Immunol. 29:665-705.*
Das 2013 Blood. 121 (17):3386-3395.*
Dong 2012 Immunity 36, 974-985.*
Gerth 2019 Front. Immunol. 10:1449, 1-11.*
Gianchecchi 2018 Front. Immunol. 9:2374, 1-12.*
Huang 2016 OncoImmunology, 6:2, e1267094, 1-12.*
Katz 2018 Cellular Immunology 327: 54-61.*
Kim (2020) Immune Netw. 20(1 ):e8, 1-15.*
Mehrle 2005 Immunology and Cell Biology 83: 33-39.*
Mehrle 2008 Molecular Immunology 45: 796-804.*
Menard 2014; J Allergy Clin Immunol 133:1149-61.*
Meyers (2020) Curr Oncol. 27(S2): 106-114.*
Nowicki 2018 Cancer J. 24(1): 47-53.*
Ren (2020) Molecular Cancer 19:19, 1-19.*

(Continued)

*Primary Examiner* — Ilia I Ouspenski
(74) *Attorney, Agent, or Firm* — Hodgson Russ LLP

(57) ABSTRACT

Provided are compositions and methods for identifying individuals with cancer who will benefit from PD-1 inhibitor therapy. The method comprises determining levels of signaling lymphocyte activation molecule-associated protein (SAP) in an individual and based on the SAP levels, determining if the individual is suitable for PD-1 inhibitor therapy. Also provided is a method of treatment of X-linked lymphoproliferative disease comprising administering to an individual PD-1 inhibitory therapy, with or without SHP2 inhibitors.

5 Claims, 26 Drawing Sheets

Specification includes a Sequence Listing.

(56) References Cited

OTHER PUBLICATIONS

Teng (2018) Cancer Letters 414: 166-173.*
Togashi 2019 Nature Reviews Clinical Oncology 16: 356-371.*
Vareki (2017) Critical Reviews in Oncology/Hematology 116: 116-124.*
Veillette (2006) Nature Reviews Immunology 6: 56-66.*
Veillette 2010 Cold Spring Harb Perspect Biol 2:a002469, 1-15.*
Wang 2017; International Immunopharmacology 46: 210-219.*
Wu 2016 Current Opinion in Immunology 38:45-51.*
Zhao 2014 PNAS 111(7): 2674-2679.*
Chen, G., et al., Signaling Lymphocyte Activation Molecule-Associated Protein is a Negative Regulator of the CD8 T Cell Response in Mice, The Journal of Immunology, Aug. 15, 2005, vol. 175, No. 4, pp. 2212-2218.
Peled, M., et al., Affinity purification mass spectrometry analysis of PD-1 uncovers SAP as a new checkpoint inhibitor, PNAS, Dec. 27, 2017, pp. E468-E477. www.pnas.org/cgi/doi/10.1073/pnas.1710437115.

* cited by examiner $g_i$ $g_{ii}$ $g_{iii}$ $h_i$ $h_{ii}$ g h i j

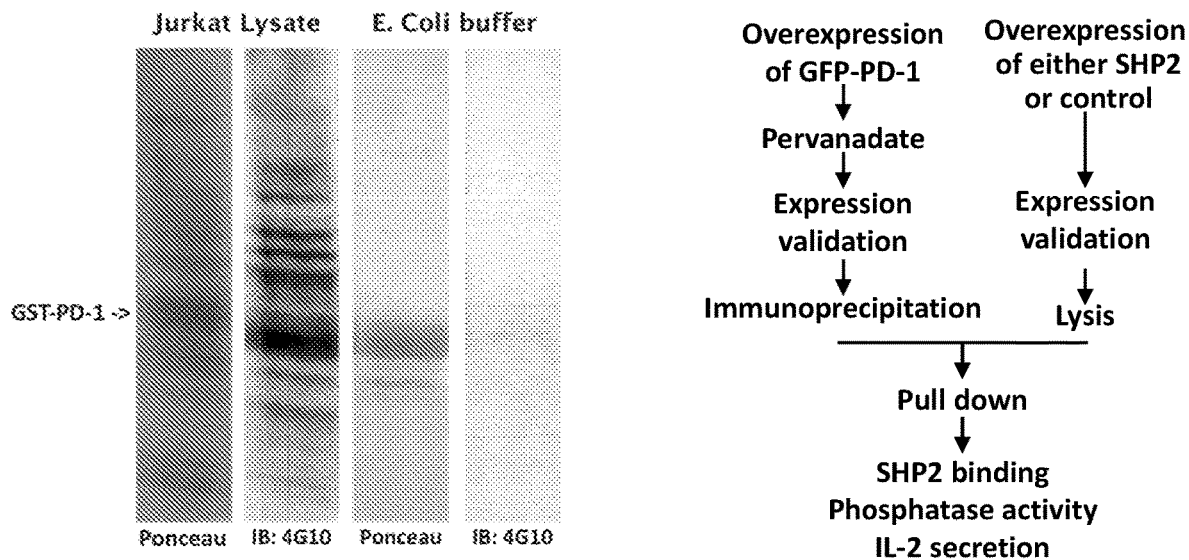
Figure 7
Figure 8
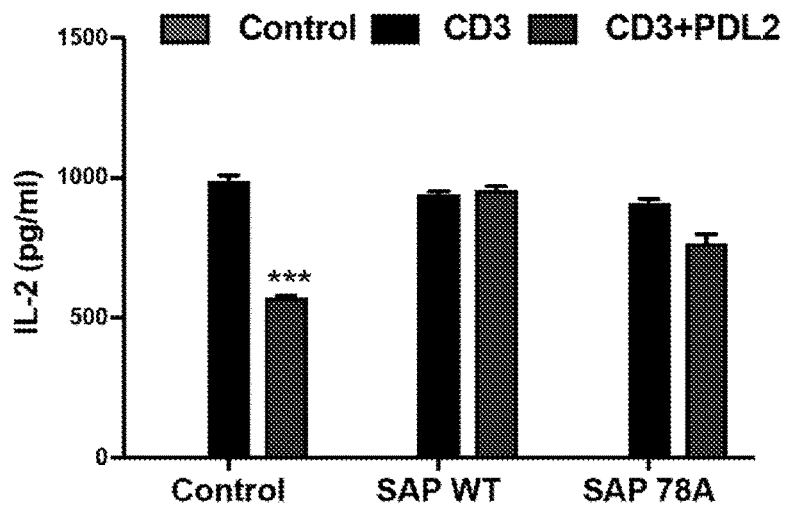
Figure 9

SEQUENCE LISTING

```
<160> NUMBER OF SEQ ID NOS: 11

<210> SEQ ID NO 1
<211> LENGTH: 11
<212> TYPE: PRT
<213> ORGANISM: Artificial Sequence
<220> FEATURE:
<223> OTHER INFORMATION: Recombinant pCD3
<220> FEATURE:
<221> NAME/KEY: MISC_FEATURE
<222> LOCATION: (6)..(6)
<223> OTHER INFORMATION: Y is phosphorylated

<400> SEQUENCE: 1

Gly His Asp Gly Leu Tyr Gln Gly Leu Ser Thr
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Recombinant pSLAMF5
<220> FEATURE:
<221> NAME/KEY: MISC_FEATURE
<222> LOCATION: (6)..(6)
<223> OTHER INFORMATION: Y is phosphorylated
```

```
<400> SEQUENCE: 2

Ser Lys Lys Thr Ile Tyr Thr Tyr Ile Met Ala
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Recombinant pCD28
<220> FEATURE:
<221> NAME/KEY: MISC_FEATURE
<222> LOCATION: (5)..(5)
<223> OTHER INFORMATION: Y is phosphorylated

<400> SEQUENCE: 3

Leu His Ser Asp Tyr Met Asn Met Thr Pro
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Recombinant pCD28
<220> FEATURE:
<221> NAME/KEY: MISC_FEATURE
<222> LOCATION: (5)..(5)
<223> OTHER INFORMATION: Y is phosphorylated

<400> SEQUENCE: 4

His Tyr Gln Pro Tyr Ala Pro Pro Arg Asp
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Peptide sequence
<220> FEATURE:
<221> NAME/KEY: MISC_FEATURE
<222> LOCATION: (8)..(8)
<223> OTHER INFORMATION: E is phosphorylated

<400> SEQUENCE: 5

Arg Arg Leu Ile Glu Asp Ala Glu Tyr Ala Ala Arg Gly
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Mutated PD-1 tail region

<400> SEQUENCE: 6

Val Asp Glu Gly Glu Leu
1               5

<210> SEQ ID NO 7
<211> LENGTH: 6
<212> TYPE: PRT
<213> ORGANISM: Artificial Sequence
<220> FEATURE:
<223> OTHER INFORMATION: Mutated PD-1 tail region

<400> SEQUENCE: 7
```

```
Thr Glu Glu Ala Thr Ile
1               5

<210> SEQ ID NO 8
<211> LENGTH: 6
<212> TYPE: PRT
<213> ORGANISM: Artificial Sequence
<220> FEATURE:
<223> OTHER INFORMATION: Mutated PD-1 tail region

<400> SEQUENCE: 8

Val Asp Phe Gly Glu Leu
1               5

<210> SEQ ID NO 9
<211> LENGTH: 6
<212> TYPE: PRT
<213> ORGANISM: Artificial Sequence
<220> FEATURE:
<223> OTHER INFORMATION: Mutated PD-1 tail region

<400> SEQUENCE: 9

Thr Glu Phe Ala Thr Ile
1               5

<210> SEQ ID NO 10
<211> LENGTH: 6
<212> TYPE: PRT
<213> ORGANISM: Artificial Sequence
<220> FEATURE:
<223> OTHER INFORMATION: Wild-type PD-1 tail region

<400> SEQUENCE: 10

Val Asp Tyr Gly Glu Leu
1               5

<210> SEQ ID NO 11
<211> LENGTH: 6
<212> TYPE: PRT
<213> ORGANISM: Artificial Sequence
<220> FEATURE:
<223> OTHER INFORMATION: Wild-type PD-1 tail region

<400> SEQUENCE: 11

Thr Glu Tyr Ala Thr Ile
1               5
```

PD-1 RELATED CANCER THERAPY

CROSS-REFERENCE TO RELATED APPLICATIONS

This application claims priority to U.S. Provisional application No. 62/608,998, filed on Dec. 21, 2017, the disclosure of which is incorporated herein by reference.

STATEMENT REGARDING FEDERALLY SPONSORED RESEARCH

This invention was made with government support under grant numbers 1R01AI125640, R01CA49152, and P30CA016087 awarded by the National Institutes of Health. The government has certain rights in the invention.

BACKGROUND OF THE DISCLOSURE

Tight control of T cell activation is essential to maintain immune homeostasis. T cell surface-expressed inhibitory receptors are key regulators that limit excessive T cell responses, and in recent years have proven to be important targets for anti-cancer therapeutics. Programmed cell death-1 (PD-1) is a critical inhibitory receptor, and in vivo and in vitro studies have documented its inhibitory function in T cells.

PD-1 is expressed on activated T and B cells, natural killer cells, monocytes, dendritic cells and melanoma cells. There are two PD-1 ligands: PD-1 ligand 1 (PD-L1; also known as B7-H1) and PD-1 ligand 2 (PD-L2; also known as B7-DC). The cytoplasmic tail of PD-1 contains two tyrosine motifs, an immunoreceptor tyrosine-based inhibitory motif (ITIM) and an immunoreceptor tyrosine based-switch motif (ITSM). Both motifs are phosphorylated upon PD-1 engagement (Sheppard et al. (2004), *FEBS letters* 574(1-3):37-41; Okazaki et al., 2001, *Proceedings of the National Academy of Sciences of the United States of America* 98(24):13866-13871). SHP2, a tyrosine phosphatase, is recruited by the cytoplasmic tail of PD-1 and is associated with dephosphorylation of key tyrosine residues or certain signaling molecules. It is considered that the ITSM, rather than the ITIM is involved in SHP2 recruitment (Chemnitz et al., 2004, *Journal of immunology* 173(2):945-954). PD-1 has recently drawn attention because of the clinical efficacy of blocking the PD-1 pathway in cancer immunotherapy. Antibodies targeting PD-1 have elicited clinical responses in multiple tumors. However, response to anti-PD-1 interventions is limited to a small fraction of patients and it is not understood prior to initiation of PD-1 therapy which individuals will respond, or not, to the treatment.

SUMMARY OF THE DISCLOSURE

The present disclosure identifies novel biomarkers which can be used to identify individuals whose tumors are likely to respond to PD-1 therapy, and new therapeutic approaches for those whose tumors are not likely to respond to PD-1 therapy.

The disclosure is based on our work in which affinity purification mass spectrometry was used to uncover multiple novel proteins associated with PD-1. Among these proteins, signaling lymphocytic activation molecule-associated protein (SAP) was functionally and mechanistically analyzed for its contribution to PD-1 inhibitory responses. Silencing of SAP augmented, while overexpression blocked PD-1 function. T cells from patients with X-linked lymphoproliferative disease (XLP), who lack functional SAP, were hyper-responsive to PD-1 signaling, confirming its inhibitory role downstream of PD-1. Strikingly, signaling downstream of PD-1 in purified T cell subsets did not correlate with PD-1 surface expression but was inversely correlated with intracellular SAP levels. Mechanistically, SAP opposed PD-1 function by acting as a molecular shield of key tyrosine residues that are targets for the tyrosine phosphatase SHP2, which mediates PD-1 inhibitory properties. Our results identify SAP as an inhibitor of PD-1 function and SHP2 as a therapeutic target in patients with XLP.

Based on our findings, this disclosure provides a method for treatment of XLP. The method comprises the steps of administering to an individual who is afflicted with XLP, an effective amount of PD-1 inhibitor, or a SHP2 inhibitor, or a combination of one or more of PD-1 inhibitors and SHP2 inhibitors.

In one aspect, this disclosure provides a method for identifying an individual afflicted with cancer, who is suitable for treatment with PD-1 inhibitors. The method comprises determination of SAP levels in individual, and if the SAP levels are at or lower than a reference value then identifying the individual as being suitable for PD-1 inhibitor therapy, and if the SAP level is higher than a reference value, then identifying the individual to be not suitable for PD-1 inhibitor therapy.

In one aspect, this disclosure provides a method of treatment of an individual with cancer comprising determining SAP level in the individual and if the SAP level is at or lower than a reference value then administering PD-1 inhibitor therapy to the individual, and if the SAP level is higher than a reference value, then treating the individual with a therapy other than PD-1 therapy, such as therapy by administration of SHP2 inhibitor, or therapies targeting inhibitory receptors such as CTLA-4, LAG-3, TIM-3, and BLTA. Monitoring of SAP levels can be carried out during PD-1 or other therapies.

In one aspect, this disclosure provides a method of evaluating the effectiveness of PD-1 therapy in an individual who is undergoing such therapy comprising monitoring SAP levels in the individual at one or more times prior to, during, and after PD-1 therapy, and based on the levels, making an assessment of the efficacy of the treatment. Increasing SAP would be indicative of the tumor likely to be losing responsiveness. The SAP levels may assist clinicians in deciding if anti-PD-1 therapy should be combined with other therapies.

BRIEF DESCRIPTION OF THE FIGURES

FIG. 7. Phosphorylation of wild type GST-PD1. Jurkat T cells were treated with pervanadate; Bacterial lysate or whole-cell lysate were subject to pull-down with the GST-tagged bait, and samples were analyzed by immunoblotting. 4G10 antibody was used to detect phosphotyrosine residues.

FIG. 8. Diagram describing the workflow of the phosphatase activity assay. GFP-PD-1 WT, GFP-PD-1 Y223F (ITIM mutant), or GFP-PD-1 Y248F (ITSM mutant) were expressed in 293 cells that were then treated with pervanadate. Next, phosphorylated GFP-PD-1 proteins obtained by GFP immunoprecipitation were mixed with lysates from cells overexpressing SHP2 and the levels of SHP2 bound to each version of PD-1 was recorded as well as its activity.

FIG. 9. SAP binding to Fyn doesn't play a role downstream of PD-1 signaling. Freshly isolated human CD3+ T cells were transfected with plasmids directing expression of different versions of SAP (WT or Q78A), or control null plasmid. After 24 hours, the cells were stimulated with magnetic beads coated with anti-CD3, or anti-CD3+PDL2 for additional 24 hours. At this time, media was collected for IL-2 (ELISA). The bars from left to right for each set are: Control, CD3, and CD3+PDL2.

DESCRIPTION OF THE DISCLOSURE

Figure 1:
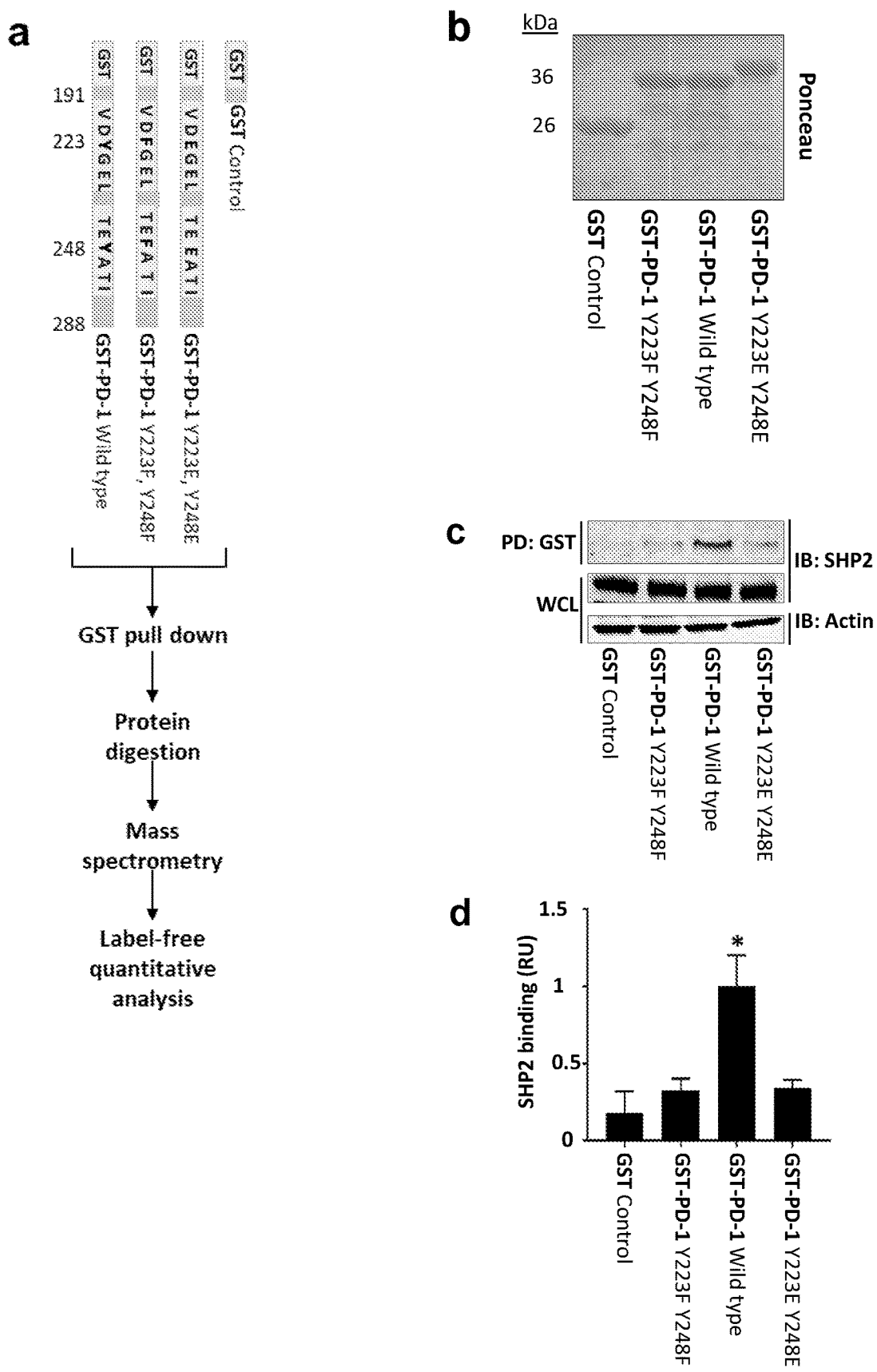
FIG. 1. Mass spectrometry based approach identifies PD-1 interacting proteins. (a) Experimental design and schematic of the different versions of the GST tagged PD-1-tails that were used as baits. (b) Ponceau staining shows the size and the amount of GST-PD-1-tail fusion protein used in each affinity purification condition. (c) Jurkat T cells were activated with pervanadate and whole cell lysates (WCL) were used for pull-down (PD) with the GST-tagged baits. Samples were analyzed by immunoblotting, as indicated (IB). (d) Densitometry values of the affinity purified SHP2 after normalized to GST expression levels. All values are fold-change compared to the intensity of SHP2 in the GST-PD-1 WT. Data are represented as mean±SEM. * represent significant differences between the denoted protein and the GST control, P<0.05, n=3, unpaired t test. (e) Summary of the workflow and the results of pull-down mass spectrometry analysis. (f) One-sided volcano plot of the PD-1 tails interacting proteins. SH2 domain containing proteins are highlighted in red, while proteins that are highlighted in orange were annotated as immune related. Proteins that are labeled in green met both conditions. (g) STRING interaction map of PD-1 and the candidate proteins identified. Line thickness indicates the strength of data to support interaction.
Figure 1:
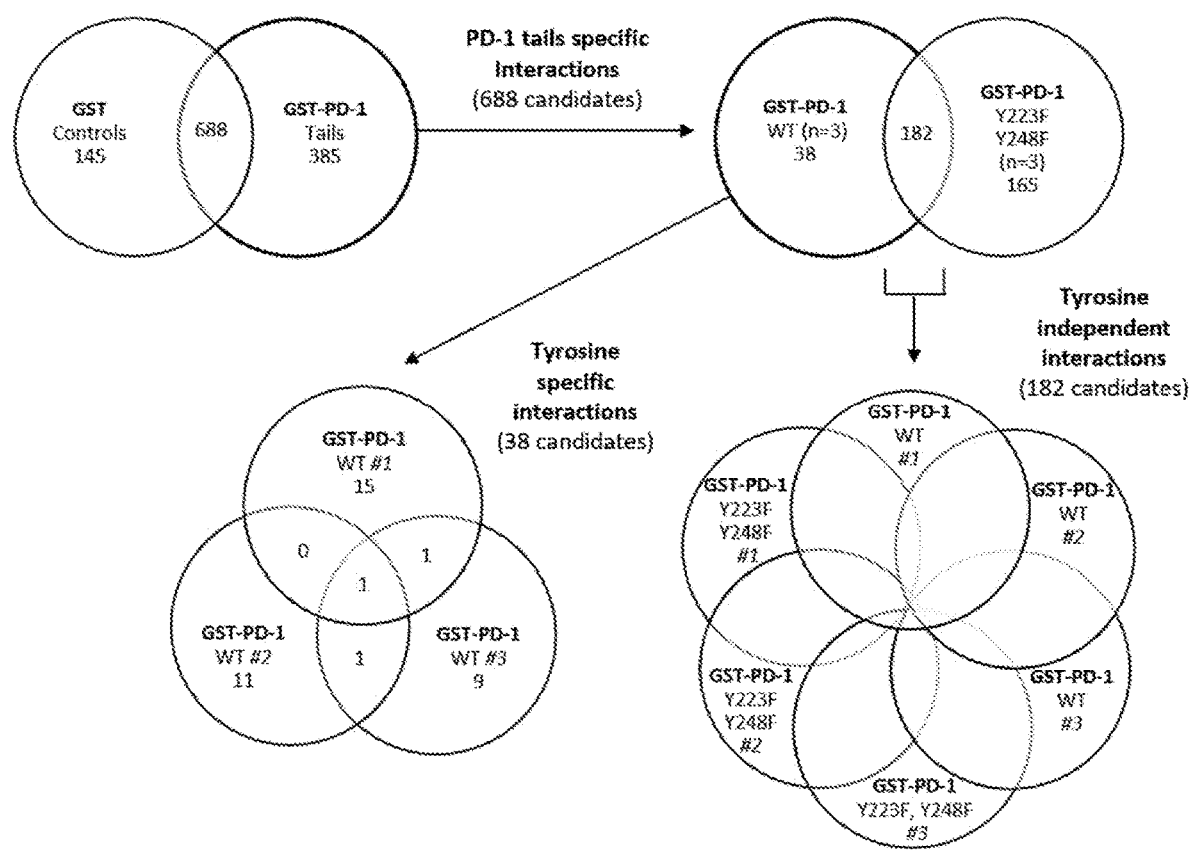
Figure 1:
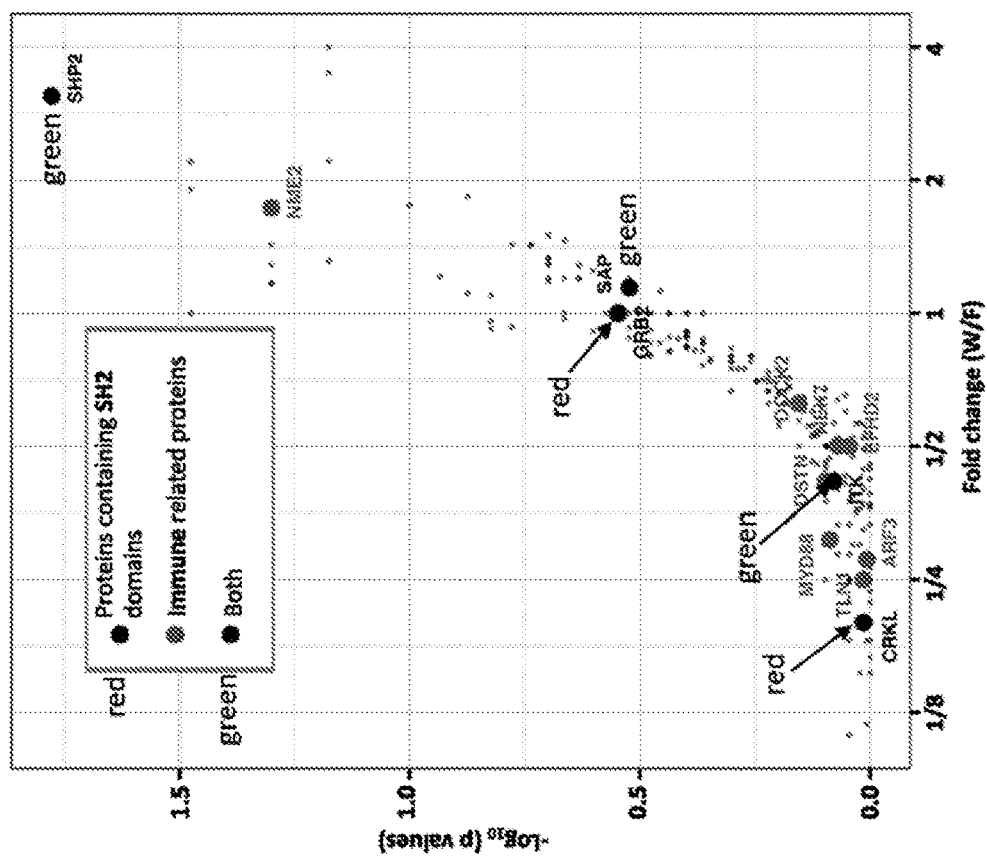

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

Every numerical range given throughout this specification includes its upper and lower values, as well as every narrower numerical range that falls within it, as if such narrower numerical ranges were all expressly written herein.

Whenever a singular term is used in this disclosure, a plural term is also included and vice-versa. For example, "a", or "an" also includes a plurality of the referenced items, unless otherwise indicated.

The present disclosure provides compositions and methods for identifying tumors that are likely to respond to PD-1 therapy and optionally, treatment of such tumors.

The present disclosure also identifies targets that interact with PD-1 in X-linked lymphoproliferative disease (XLP), and provides compositions and methods for treatment of XLP.

To uncover novel intracellular proteins that interact with PD-1, we used the PD-1 cytoplasmic tail as a bait to affinity purify candidate proteins in activated human T cells, followed by identification with high-resolution mass spectrometry (MS). In addition to SHP2, we discovered several other PD-1 interacting partners, including the signaling lymphocytic activation-molecule (SLAM) associated protein (SAP), also known as SH2D1A (SH2 domain-containing protein IA). Interestingly, SAP blocked PD-1 inhibitory functions in T cells (such as adhesion, proliferation, and cytokine secretion) through indirect inhibition of SHP2 activity. Accordingly, interventions at the level of the PD-1/SAP pathway may provide a novel mechanism to enhance T cell responses and thus optimize the treatment of malignancies, immunodeficiencies and chronic infections.

We discovered that SAP indirectly inhibits PD-1 function by shielding tyrosine residues from SHP2 activity. Furthermore, while we confirmed previous observations that the PD-1 ITIM and ITSM are both required for maximal SHP2 binding to PD-1, we found that ITIM is critically required for SHP2 phosphatase activity as well. Collectively, through a series of biochemical investigations and immune based assays, we have identified SAP as an inhibitor of PD-1 function, and these novel insights into PD-1 biology form the basis for therapeutic strategies targeting the PD-1/SHP2 axis.

XLP can be diagnosed in individuals by standard diagnostic criteria known in the art. For example, a genetic test to evaluate the presence or absence of functional SAP within immune cells may be used. XLP can be diagnosed based on clinical assessment. Further, a test based on detecting mutations in SH2D1A can be used. An example is a test that is commercially available (such as, from LabCorp).

In one aspect, this disclosure provides a method for treatment of XLP comprising administering to an individual in need of treatment a composition comprising an effective amount of programmed cell death-1 (PD-1) inhibitor and/or SIP2 inhibitor. The PD-1 inhibitor may be an agent that inhibits PD-1, such as an antibody against PD-1, or it may be an agent that inhibits one of the ligands for PD-1, such as an antibody against PD-L1. The dosage of the PD-1 inhibitor and the frequency of administration and the length of treatment can be decided by the treating physician. Examples of inhibitors of PD-1 include pembrolizumab and nivolumab, and examples of inhibitors PD-L1 include atezolizumab, avelumab, and durvalumab. Generally, a therapeutically effective amount of an antibody or a composition described herein can be in the range of 0.1 mg/kg to 100 mg/kg and all values therebetween. For example, it can be 0.1 mg/kg to 50 mg/kg. As an example, nivolumab can be given 8 mg/kg every two weeks (total 160-240 mg). As another example, Pembrolizumab may be given in the same range (usually 200 mg fixed dose).

Many SHP2 inhibitors are known in the art. These include the SHP2 inhibitors disclosed in PCT/IB2015/050345 (published as WO2015107495), PCT/IB2015050344 (published as WO2015107495), PCT/IB2015/050343 (published as WO2015107493), US publication no. 20170342078, Xie et al., (J. Medicinal Chem., DOI: 10.1021/acs.jmedchem. 7b01520, November 2017), LaRochelle et al., (25(24): 6479-6485, 2017). The listing and descriptions of SHP2 inhibitors from these published applications and publications are incorporated herein by reference. Examples of SHP2 inhibitors include, but are not limited to, TNO155, 1-(4-(6-bromonaphthalen-2-yl)thiazol-2-yl)-4-methylpiperidin-4-amine, and chemical compounds having a benzothiazolopyrimidones scaffold, NSC-117199, NSC-87877, SPI-112, SPI-112Me, Fumosorinone, demethylincisterol $A_3$, 11a-1, and Cryptotanshinone. Expression of the gene PTPN11 encoding SHP2 can also be inhibited by the use of inhibitory RNAs, such as siRNA, shRNA, CRISPR/Cas9 or other gene expression disrupters. Generally, an amount of from 1 µg/kg to 100 mg/kg and all values therebetween may be used.

The term "therapeutically effective amount" as used herein refers to an amount of an agent sufficient to achieve, in a single or multiple doses, the intended purpose of treatment. Treatment does not have to lead to complete cure, although it may. Treatment can mean alleviation of one or more of the symptoms or markers of the indication. The exact amount desired or required will vary depending on the particular compound or composition used, its mode of administration, patient specifics and the like. Appropriate effective amount can be determined by one of ordinary skill in the art informed by the instant disclosure using only routine experimentation. Within the meaning of the disclosure, "treatment" also includes relapse, or prophylaxis as well as the alleviation of acute or chronic signs, symptoms and/or malfunctions associated with the indication. Treatment can be orientated symptomatically, for example, to suppress symptoms. It can be effected over a short period, over a medium term, or can be a long-term treatment, such as, for example within the context of a maintenance therapy. Administrations may be intermittent, periodic, or continuous.

Where a range of values is provided in this disclosure, it should be understood that each intervening value, to the tenth of the unit of the lower limit between the upper and lower limit of that range, and any other intervening value in that stated range is encompassed within the invention, unless clearly indicated otherwise. The upper and lower limits of these smaller ranges may independently be included in the smaller ranges encompassed within the disclosure.

The pharmaceutical compositions may be in the form of solutions, suspensions, emulsions, and solid injectable compositions that are dissolved or suspended in a solvent immediately before use. The injections may be prepared by dissolving, suspending or emulsifying one or more of the active ingredients in a diluent. Examples of diluents are distilled water for injection, physiological saline, physiologic buffer, vegetable oil, alcohol, and a combination thereof. Further, the compositions may contain stabilizers, solubilizers, suspending agents, emulsifiers, soothing agents, buffers, preservatives, etc. The pharmaceutical compositions may be formulated into a sterile solid or powdered preparation, for example, by freeze-drying, and may be used after sterilized or dissolved in sterile injectable water or other sterile diluent(s) immediately before use. The compositions can include one or more standard pharmaceutically acceptable carriers. Some examples herein of pharmaceutically acceptable carriers can be found in: *Remington: The Science and Practice of Pharmacy* (2013) 22nd Edition, Pharmaceutical Press.

The pharmaceutical composition of the invention may be administered via any route that is appropriate, including but not limited to oral, parenteral, sublingual, transdermal, rectal, transmucosal, topical, via inhalation, via buccal administration, or combinations thereof. Parenteral administration includes, but is not limited to, intravenous, intraarterial, intraperitoneal, subcutaneous, intramuscular, intrathecal, and intraarticular. The agents(s) can also be administered in the form of an implant, which allows a slow release of the compound(s), as well as a slow controlled i.v. infusion.

In one aspect, this disclosure provides a method for identifying if an individual having cancer is suitable for (or is likely to benefit from) treatment with PD-1 inhibitors (directed to PD-1 or PD-L1 or PD-L2). The suitability is determined by measurement of SAP levels in individual. If the SAP levels are at or lower than a reference value, the individual is identified as being suitable for PD-1 inhibitor therapy, and if the SAP level is at or higher than a reference value, then the individual is identified as not being suitable for PD-1 inhibitor therapy. In embodiments, a lower SAP level may be a 5%, 10%, 20%, 25%, 30%, 40%, 50% or more decrease over normal levels. In an embodiment, a lower SAP level may be a level that is considered to be clinically lower than normal SAP levels. In an embodiment, a lower SAP level may be a level that is considered to be significantly lower than normal SAP levels. SAP levels, including reference levels, can be measured at the protein or at the nucleic acid (e.g., mRNA) level. For example, primers can be designed based on the known sequence of SAP protein and mRNA measured after PCR. Alternatively, antibodies to SAP can be used in immunological measurements such as ELISA, Western blots or flow cytometry. A monoclonal antibody, XLP-1D12, to human SAP is available commercially from Thermo Fisher Scientific. SAP levels can be measured in biological fluid samples, such as in, for example blood cells. Peripheral blood cells or peripheral T-cells can be used. SAP levels can also be measured in tissues, such as tumor biopsy samples. Reference value for SAP levels can be obtained from one or more normal individuals who do not have the indication.

Suitable cancers that may be diagnosed for PD-1 treatment suitability and treated with PD-1 therapy include any cancer that is generally treatable with checkpoint inhibitors. Examples include, but are not limited to, melanoma of the skin, non-small cell lung cancer, kidney cancer, bladder cancer, head and neck cancers, and Hodgkin lymphoma, other urinary tract cancers, and other types of cancers.

In one aspect, this disclosure provides a method of treatment of an individual with cancer comprising determining SAP level in the individual and if the SAP level is lower than a reference value then administering PD-1 inhibitor therapy to the individual, and if the SAP level is at or higher than a reference value, then treating the individual with a therapy other than PD-1 therapy. For example, the individual may then be treated with a SHP2 inhibitor, or other therapeutic approaches such as targeting of CTLA-4, LAG-3, TIM-3, and BLTA as well as inhibiting myeloid derived suppressor cells, tumor associated macrophages and Treg cells may be used.

In as aspect, this disclosure provides a method for identifying agents that can inhibit (or enhance) the function of SAP and thereby induce or suppress the immune response.

The invention is further described through the following example, which is intended to be illustrative, and not restrictive.

EXAMPLE 1

Results

Mass Spectrometry-Based Approach Identifies PD-1 Interacting Proteins.

The identification of proteins associated with transmembrane receptors by affinity purification can be challenging due to the extraction conditions needed to solubilize receptors, to which the relevant complexes are labile. To overcome this limitation, we utilized GST-tagged versions of the PD-1 cytoplasmic tail (97 amino acids long) to affinity purify intracellular proteins from lysates of Jurkat T cells (FIG. 1a). To differentiate between phosphotyrosine-dependent and independent interactions, we used an unmodified PD-1 tail (WT; wild type), a phosphodeficient version in which the tyrosine residues were substituted with phenylalanines (Y223F, Y248F), or a "phosphomimetic" version in which both tyrosine residues were substituted with glutamic acid (Y223E, Y248E) to serve as baits for PD-1-interacting proteins. The GST-PD-1 tails were mixed with lysates from activated T cells and associated proteins were identified by MS. Label-free relative quantitative analysis using spectral counts was performed to determine the amount of each protein that interacted with the respective GST fusion proteins. SHP2 is the only protein reported to interact strongly with the tail of PD-1. As expected, based on the phosphotyrosine dependence of the SHP2/PD1 interaction, although each bait was present at similar amounts in the various experimental conditions (FIG. 1b), it was mainly the GST-PD-1 WT version that pulled down the highest amount of SHP2 (FIGS. 1i and 1d). Since the Y223E, Y248E version of PD-1 demonstrated inferior binding to SHP2 compared to the WT protein, we excluded this condition from our MS analysis. Western blot analysis confirmed that the pulled down GST-PD-1 WT was phosphorylated after mixing with the cell lysate (FIG. 7), while the MS analysis also confirmed that WT PD-1 was phosphorylated. Therefore, the WT version of the tail of PD-1 could reliably serve as a proxy for the activated PD-1.

To identify PD-1 tail specific interactions, we excluded proteins that were affinity purified by the GST protein itself (GST control) (FIG. 1e). Proteins that were affinity purified by GST-PD-1 Y223F, Y248F were designated as PD-1 tyrosine-independent candidates (182 candidates) (FIG. 1e). Proteins that were detected only by the GST-PD-1 WT baits were regarded as potential tyrosine-specific interactors (38 candidates) (FIG. 1e). Importantly, SHP2, the only protein known to interact with the tail of PD-1, was affinity-purified by all three replicates of the GST-PD-1 WT, but not by the GST alone nor the GST-PD-1 Y223F, Y248F tails.

We next sought to identify additional proteins that were preferentially affinity-purified by GST-PD-1 WT over GST-PD-1 Y223F, Y248F. Because the phosphorylated tyrosine residues of PD-1 are part of the ITIM and ITSM that interact preferentially with SH2 domains, we sorted our candidate interactors into proteins containing SH2 domains (UniProt) (FIG. 1f). Based on the cellular expression and the function of PD-1, we further narrowed our considerations to proteins that were annotated as immune-related according to the Mouse Genome Informatics database, which contains annotations of the phenotypes of knockout mice (FIG. 1f). Accordingly, 13 PD-1 binding proteins were identified. SHP2 demonstrated the highest binding selectivity toward WT baits, recapitulating previous observations of SHP2 interaction with the ITSM of PD-1 (FIG. 1f). Interestingly, STRING analysis (Szklarczyk D, et al. (2015) *Nucleic acids research* 43 (Database issue: D447-452) revealed that some of the proteins could interact indirectly with PD-1 through SHP2 (PTPN11) (FIG. 1g). We also observed that the adaptor protein SAP was preferentially associated with WT PD-1.

The ITIM of PD-1 is Necessary for SHP2 Activity.

Figure 2:
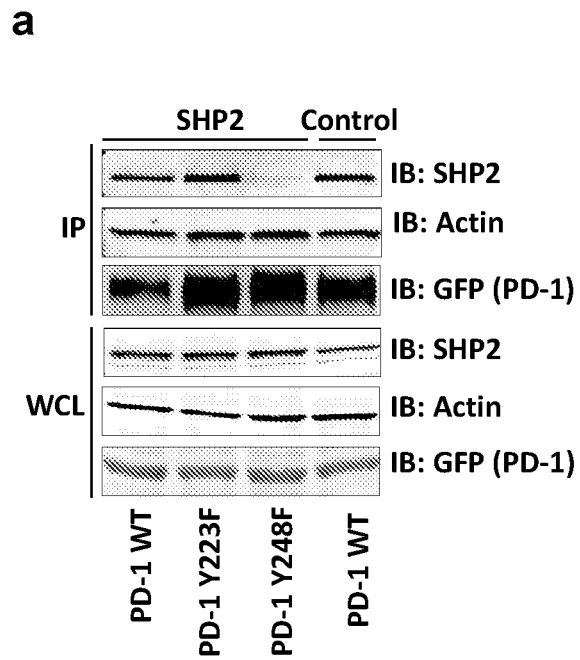
FIG. 2. The ITIM of PD-1 is necessary for SHP2 activity. (a-c) 293T cells were transfected with the indicated versions of GFP-tagged PD-1, followed by pervanadate treatment and immunoprecipitation using anti-GFP mAb-agarose. SHP2 levels bound to precipitated GFP-PD-1 were quantified (b) and subjected to phosphatase activity assay (c). Values of pulled-down SHP2 were normalized to GFP expression levels. All values are fold-change compared with the intensity of precipitated SHP2 in the WT PD-1 GFP in the SHP2 expressing cells. Phosphatase activity values are fold-change compared with the activity of immunoprecipitated SHP2 in the WT PD-1 GFP from the SHP2 expressing cells. (d-e) Jurkat T cells were transfected with GFP control or different versions of GFP-tagged PD-1 as indicated, followed by stimulation with magnetic beads coated with anti-CD3, or anti-CD3+PDL2 for additional 24 hours. Media was collected for IL-2 and IFN-γ measurements (ELISA). (f) The "two-step activation" model. SHP2 is first recruited to the ITSM (step 1), and only then the second SH2 binds to the ITIM (Step 2), which opens the catalytic domain of SHP2 to the fully active conformation. Data are represented as mean±SEM.  or * represent significant differences between the denoted group and the PD-1 WT in c and d, or between the denoted group and the anti-CD3 treated cells in e and f; ** $P<0.01$, * ** $P<0.001$, n=3, unpaired t test. For FIGS. 2d, and 2e, the bars from left to right for each set are: Control, CD3, and CD3+PDL2.
Figure 2:
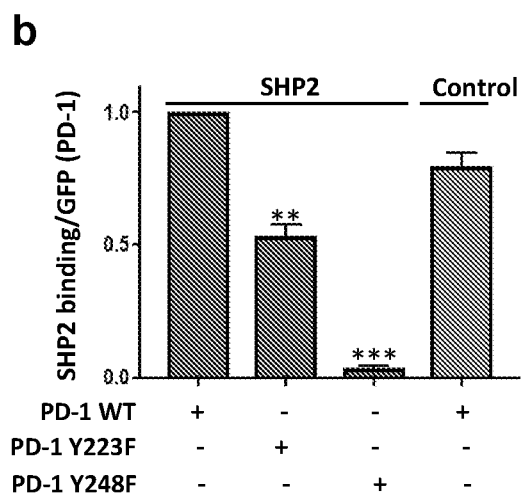
Figure 2:
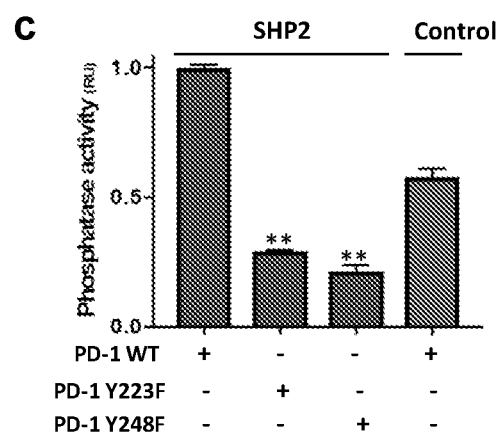
Figure 2:
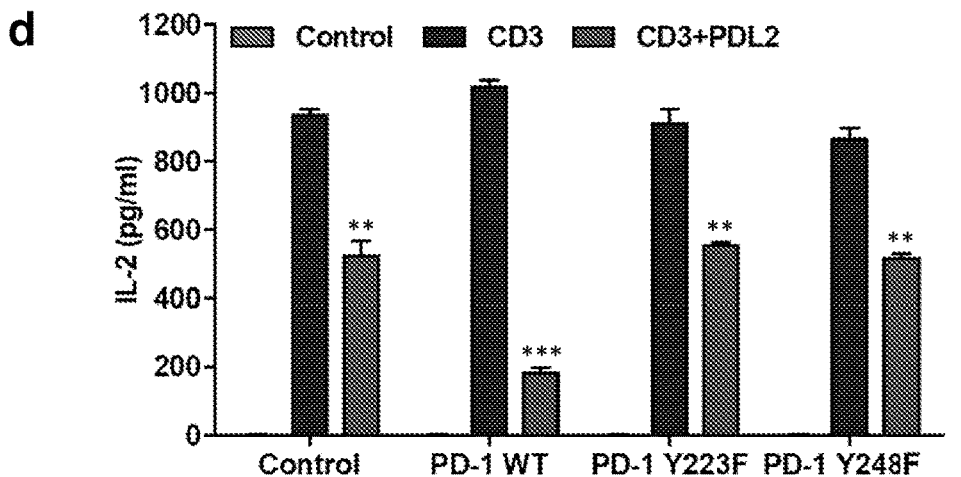
Figure 2:
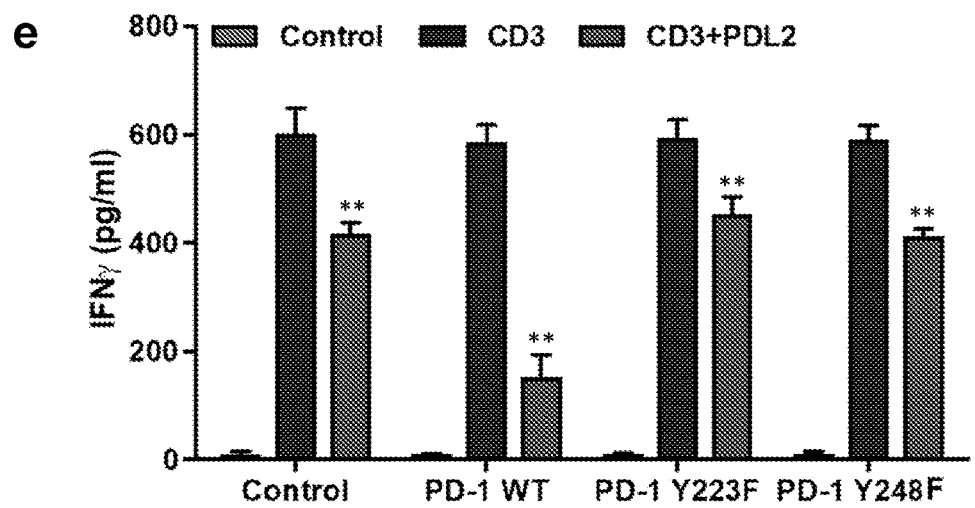
Figure 2:
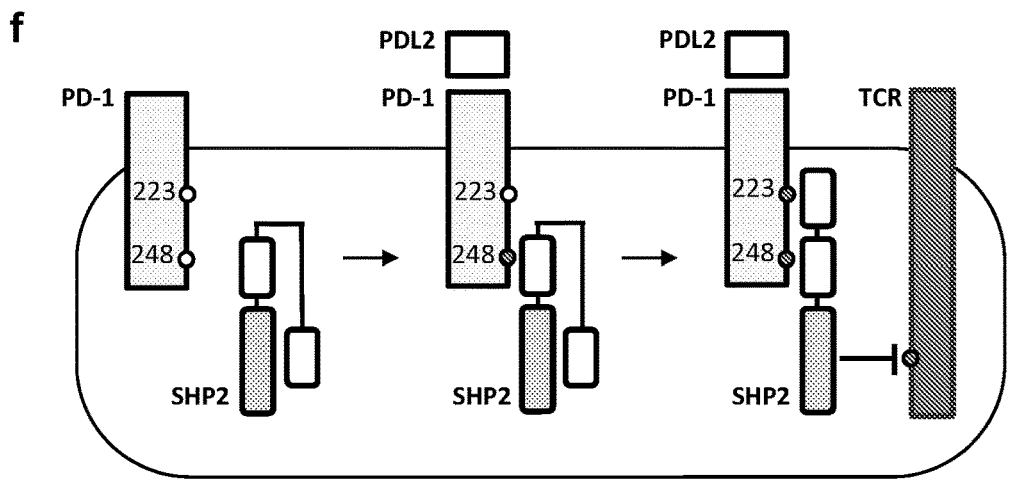

While the contribution of the ITSM of PD-1 to SHP2 binding and downstream signaling is established, the role of the ITIM in PD-1 function is less clear. Because SHP2 has two SH2 domains and could thus potentially bind to two sequential phosphotyrosines (one tyrosine in the PD-1 ITSM and the other tyrosine in the PD-1 ITIM), we hypothesized that the ITIM of PD-1 might facilitate PD-1 signaling by stabilizing SHP2 in an open conformational state. To test this possibility, we expressed GFP-PD-1 WT, GFP-PD-1 Y223F (ITIM mutant), or GFP-PD-1 Y248F (ITSM mutant) in cells that were then treated with pervanadate (a diagram describing the experiment is provided in FIG. 8). Next, we combined the phosphorylated GFP-PD-1 proteins obtained by GFP immunoprecipitation with lysates from cells overexpressing SHP2, and recorded the levels of SHP2 bound to each version of PD-1 as well as its specific enzymatic activity. As expected, SHP2 failed to bind to PD-1 when the ITSM (Y248F) was mutated (FIG. 2a). Notably, the mutant version of the ITIM (Y223F) inhibited SHP2 binding only to a limited extent (FIG. 2b). However, SHP2 phosphatase activity assay, analyzed on the beads that were used for affinity purification of SHP2, revealed that both the ITIM and the ITSM were equally indispensable for the enzymatic activity (FIG. 2c). When Jurkat T cells that expressed different versions of GFP-tagged PD-1 were stimulated with magnetic beads coated with anti-CD3+PDL2-Fc for 24 hours, both the ITIM and the ITSM were required for PD-1 signaling to inhibit IL-2 (FIG. 2d) and IFN-γ (FIG. 2e) secretion. Thus, we propose a two-step activation model in which under resting conditions SHP2 is folded in an auto-inhibited conformation (FIG. 2f; left panel). Upon binding of a ligand (such as PDL2) to PD-1, SHP2 is recruited to the phosphorylated ITSM (FIG. 2f; middle panel—first step). However, the ITIM must also be phosphorylated to unfold SHP2 to its active conformation (FIG. 2f; right panel—second step).

SAP is Indirectly Associated with PD-1.

Figure 3:
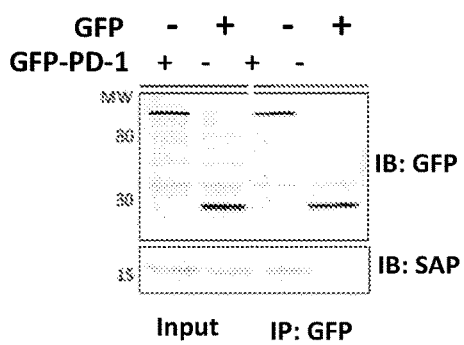
FIG. 3. SAP is indirectly associated with PD-1. ($a_i$) Pervanadate treated Jurkat T cells were transiently transfected with GFP-tagged PD-1 or GFP alone; Whole cell lysates (WCL) were immunoprecipitated with an anti-GFP antibody (IP: GFP), and samples were analyzed by immunoblotting. ($a_{ii}$) Densitometry values of data shown in $a_i$. (b) Jurkat T cells were transfected with plasmids directing expression of the indicated fluorescent proteins and after 24 hours cells were stimulated with anti-CD3 antibodies and recombinant PDL2, followed by live-imaging. Bar, 10 μm. Line analysis shows fluorescent intensities of SAP (red) along the diameter of the cell. (c) Percentage of cells showing SAP localization at the membrane or the cytosol, in the unstimulated (upper graph) and stimulated (CD3 or CD3+PDL2) conditions. ($d_i$) Jurkat T cells were transfected with different versions of GFP-tagged PD-1, as indicated, followed by treatment with pervanadate; Whole-cell lysates (Input) were immunoprecipitated with an anti-GFP antibody (IP: GFP), and samples were analyzed by immunoblotting. ($d_{ii}$ and $d_{iii}$) Densitometry values of data shown in $d_i$. ($e_i$) 293T cells were transfected with plasmid directing expression of GFP-SAP or a control GFP plasmid, followed by treatment with pervanadate; Lysates were pulled-down with the GST-tagged PD-1 and samples were analyzed by immunoblotting. ($e_{ii}$) Densitometry values of data shown $e_i$. ($f_i$) increasing concentrations of recombinant SAP were added to SAP KD Jurkat cells followed by affinity-purification with GST-PD1 and immunoblot analysis. ($f_{ii}$) Densitometry values of data shown in $f_i$. ($g_i$) SHP2 KD and scrambled control Jurkat T cells were transfected with GFP-tagged PD-1, followed by treatment with pervanadate; Lysates were immunoprecipitated with an anti-GFP antibody (IP: GFP), and samples were analyzed by immunoblotting. ($g_{ii}$ and $g_{iii}$) Densitometry values of data shown in $g_i$. ($h_i$) His tagged SAP and GST tagged SHP2 catalytic domain were incubated in the presence or absence of Jurkat T cell lysate (Control Lysate). SAP was pulled-down with nickel beads. Samples were analyzed by immunoblot. ($h_{ii}$) Densitometry values data shown in $h_i$. Data are represented as mean±SEM. *,  or * represent significant differences between the denoted condition and GFP-PD1 WT in b, between the denoted condition and the cells with cytosolic distribution of SAP in c and between the denoted condition and the control where only two groups are tested. * $P<0.05$,  $P<0.01$, * $P<0.001$, n=3, unpaired t test.
Figure 3:
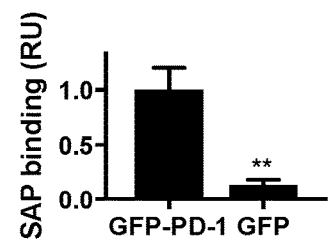
Figure 3:
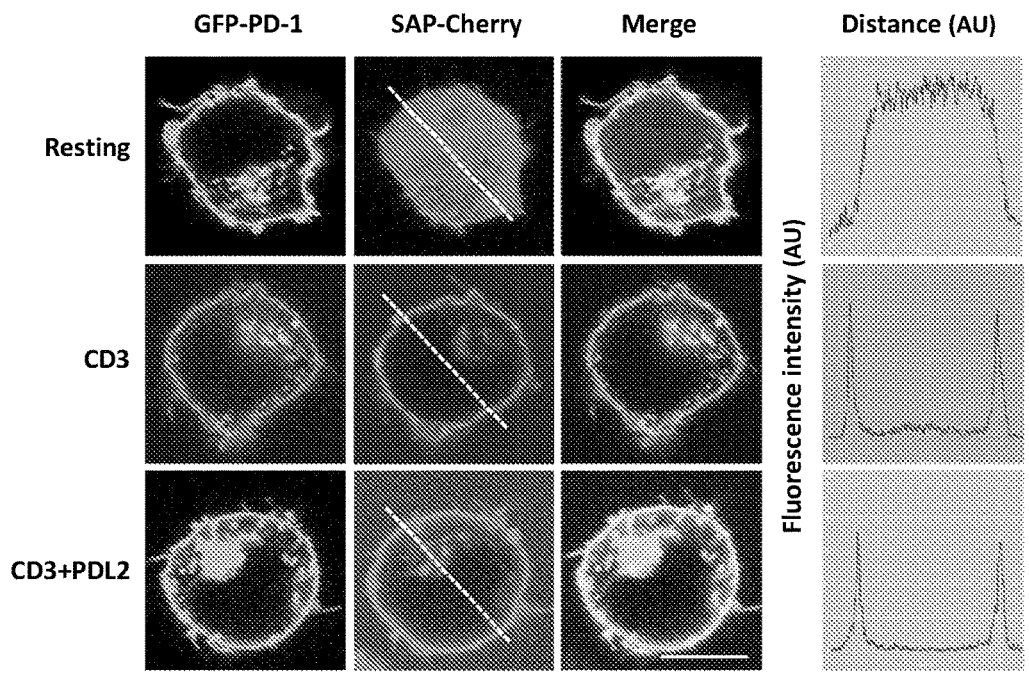
Figure 3:
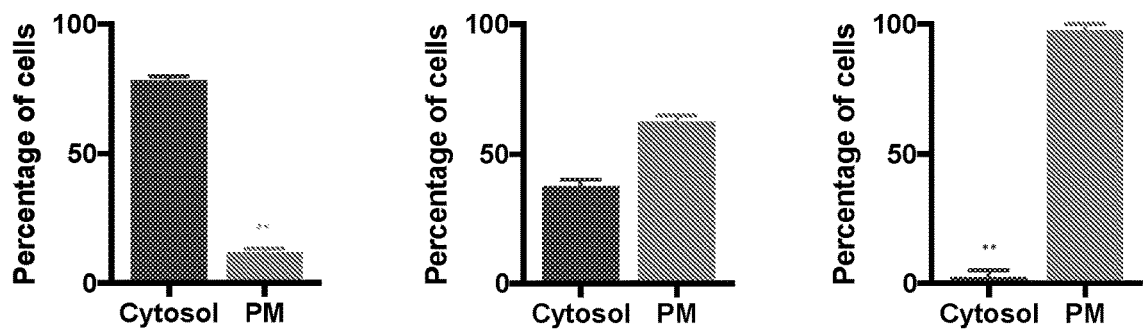
Figure 3:
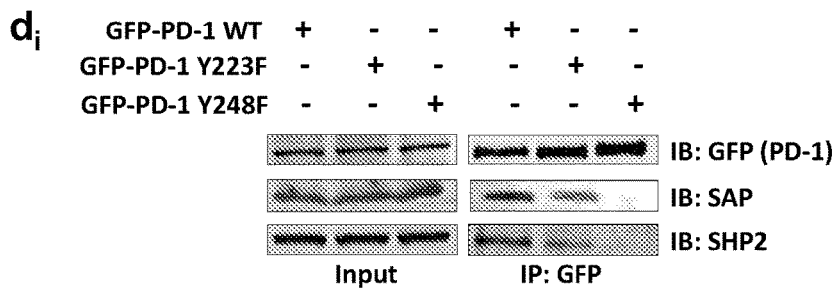
Figure 3:
Figure 3:
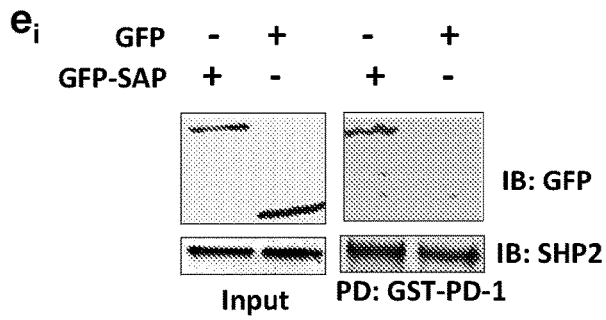
Figure 3:
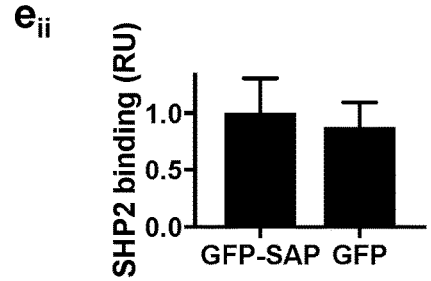
Figure 3:
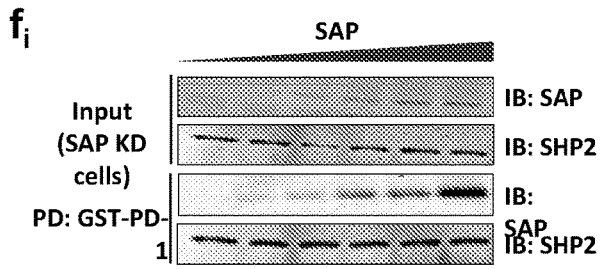
Figure 3:
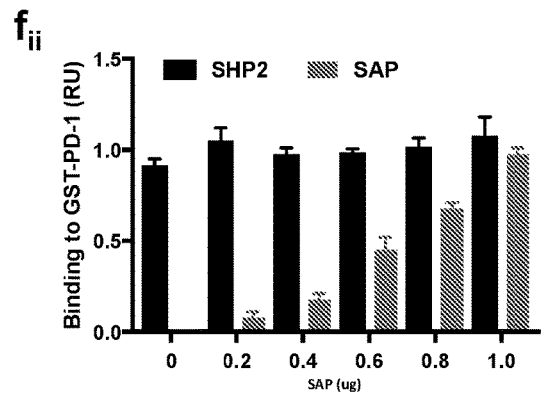
Figure 3:
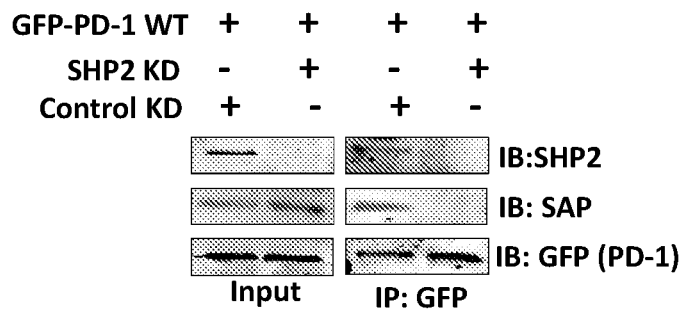
Figure 3:
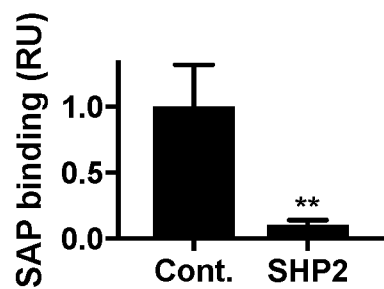
Figure 3:
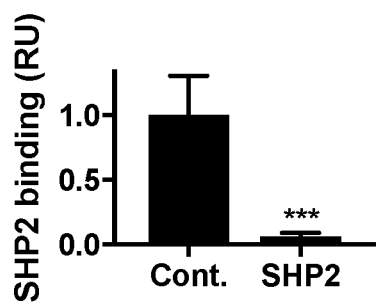
Figure 3:
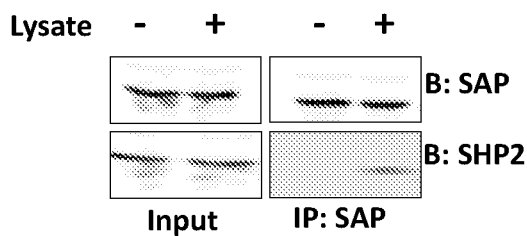
Figure 3:
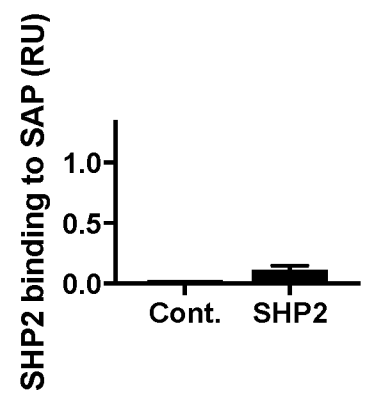

SAP is a 128-amino acid protein with a single SH2 domain that interacts with receptors of the SLAM family, through binding to phosphorylated ITSMs (Veillette A (2010) *Cold Spring Harbor perspectives in biology* 2(3): a002469). Co-immunoprecipitation experiments, in which lysates of Jurkat T cells expressing GFP-tagged PD-1 (or GFP alone) 15 were immunoprecipitated with an anti-GFP antibody, revealed that endogenous SAP is found in the same signaling complex as PD-1 (FIGS. $3a_i$ and $3a_{ii}$). In addition, overexpressed GFP-PD-1 and SAP-Cherry were found at the same sub-cellular compartment, at the plasma membrane of activated T cells (FIGS. 3b and 3c). Notably, SAP was recruited to the plasma membrane even with TCR activation alone (anti-CD3 stimulation), which is plausible considering that SAP is known to interact with additional membrane proteins, including the CD3(chain. As mentioned, SAP is known to interact with phosphorylated tyrosines present within the cytoplasmic tails of the SLAM family receptors, where it might compete with SHP2 for binding. To test if this was also the case for PD-1, WT or mutant versions of GFP-PD-1 were expressed and immunoprecipitated from activated T cells. Western blot analysis revealed that both SAP and SHP2 were associated with WT GFP-PD-1 and with GFP-PD-1 Y223F, but not with GFP-PD-1 Y248F (FIG. $3d_i$-$3d_{iii}$). Thus, it was the PD-1 ITSM, and not the ITIM, that enabled interaction with both SAP and SHP2. Next, we hypothesized that SAP inhibits PD-1 function by competing with SHP2 for binding to the PD-1 tail. To test that we performed a competitive binding assay, where overexpressed GFP-SAP competed with endogenous SHP2 on binding to GST-PD1. As shown, SAP overexpression failed to decrease the levels of SHP2 binding to PD-1, ruling out direct competition between SHP2 and SAP on direct binding to PD-1 (FIGS. $3e_i$ and $3e_{ii}$). In addition, increasing concentrations of recombinant SAP did not interfere with the affinity-purification of SHP2 by GST-PD1 (FIGS. $3f_i$ and $3f_{ii}$). To test the possibility that SAP was associated with PD-1 indirectly via its association with SHP2, we knocked down SHP2 in Jurkat T cells and observed that SAP completely failed to bind to PD-1 (FIG. $3g_i$-$3g_{iii}$). These findings suggest that SAP is associated with PD-1 indirectly, possibly through a complex with SHP2 and other adaptor proteins. Notably, the ability of SAP to bind to FYN was not necessary for its ability to inhibit PD-1 signaling and IL-2 secretion (FIG. 9) because a mutant version of SAP (SAP R78A), that cannot bind to FYN, could still inhibit PD-1 function.

Figure 10:
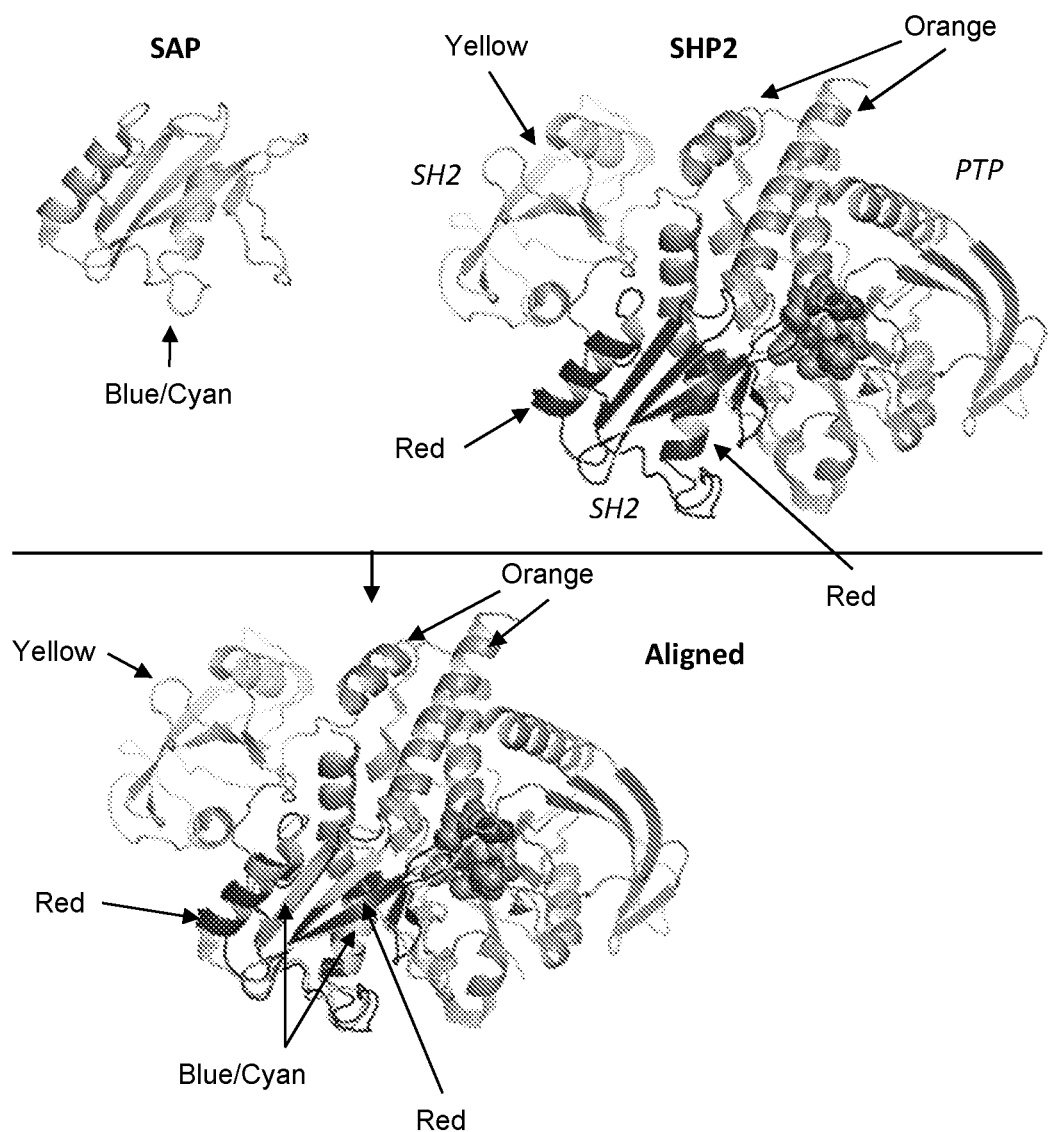
FIG. 10. Alignment of SHP2 and SAP. Figure generated with PyMOL (http://www.pymol.org) using the Protein Data Bank (PDB) codes 4DGP (SHP2) and 1M27 (SAP). Red: n-term SH2 domain of SHP2. Yellow: 2nd SH2 domain of SHP2. Orange: phosphotyrosine phosphatase domain of SHP2. Blue/Cyan: SAP. The SHP2 is in the closed conformation.

SHP2 is self-inhibited by its N-terminal SH2 (N-SH2) domain, which folds over its catalytic domain (FIG. 2f) (Pluskey et al., *The Journal of biological chemistry* 270(7): 2897-2900; Sun et al. (2013) *Nature communications* 4:2037). SAP and the N-SH2 domain of SHP2 perfectly aligned structurally (FIG. 10), suggesting that SAP might interact with and inhibit the SHP2 catalytic domain directly. To test this possibility, His-tagged SAP and GST-tagged SHP2$^{PTP}$ (the catalytic domain of SHP2) were used in co-affinity enrichment experiments, which showed a lack of direct interaction between these proteins (FIGS. $3h_i$ and $3h_{ii}$). However, these recombinant proteins were physically associated in the presence of wild type T cell (control) lysate ($3h_i$ and $3h_{ii}$), suggesting that additional proteins are required to support the association.

SAP Inhibits SHP2 Activity.

Figure 4:
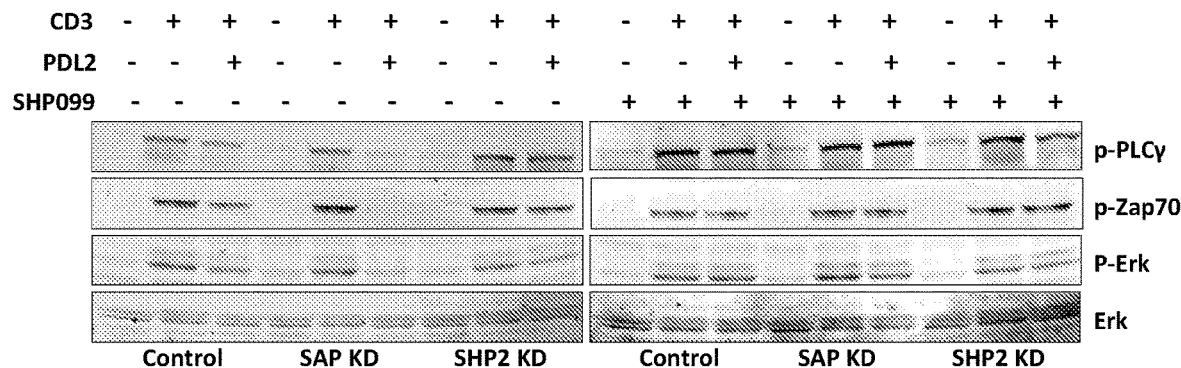
FIG. 4. SAP inhibits SHP2 activity. (a) Jurkat T cells stably transfected with shRNA for SAP (SAP KD), SHP2 (SHP2 KD) and non-targeting control (Control) were treated for one hour with SHP099 (10 uM), followed by stimulation with magnetic beads coated with anti-CD3, or anti-CD3+PDL2 for 5 minutes. At this time, the cells were harvested, and analyzed by immunoblotting, as indicated. (b) Jurkat T cells, transfected with siRNA for SAP (SAP KD) and non-targeting control (Control), were treated with pervanadate to induce maximal phosphorylation, followed by five serial washes, lysis and diafiltration to remove the drug and to exchange the buffer to a phosphatase-compatible buffer. $SHP2^{PTP}$ (GST tagged SHP2 catalytic domain) was then added to the cell lysates for one hour, at the indicated concentrations, followed by immunoblotting with anti-phosphotyrosine antibody (4G10). (c) Densitometry values of all the phophotyrosine containing proteins shown at b. All values are relative to the baseline condition (without $SHP2^{PTP}$). (d) Jurkat T cells were treated with SHP099 (10 uM), followed by affinity purification with a his-tagged SAP or his-Fab control and immunoblot analysis with anti-phosphotyrosine antibody (4G10). (e-g) Enzymatic activity of $SHP2^{PTP}$ was measured using a Malachite Green assay, with p60-SRC (e), SLAMF5 Y279 (f), CD3 Y142 (g), CD28 Y172 (h), and CD28 Y190 (i) peptides as substrates. Substrate titrations of SHP2P (dark circles) at baseline (control), or in the presence of SAP 1 uM (white circles) or SAP 10 uM (crossed circles) are shown. Curves are fitted using the Michelis-Menten equation and derived Km values are shown. The data points represent the mean of three measurements. (j) A diagram describing the shielding model. Data are represented as mean±SEM. * or ** represent significant differences between the denoted group and the anti-CD3 treated cells in a, or between SAP deficient cells and control cells in e; * <0.05, ** $P<0.01$, n=4, unpaired t test.
Figure 4:
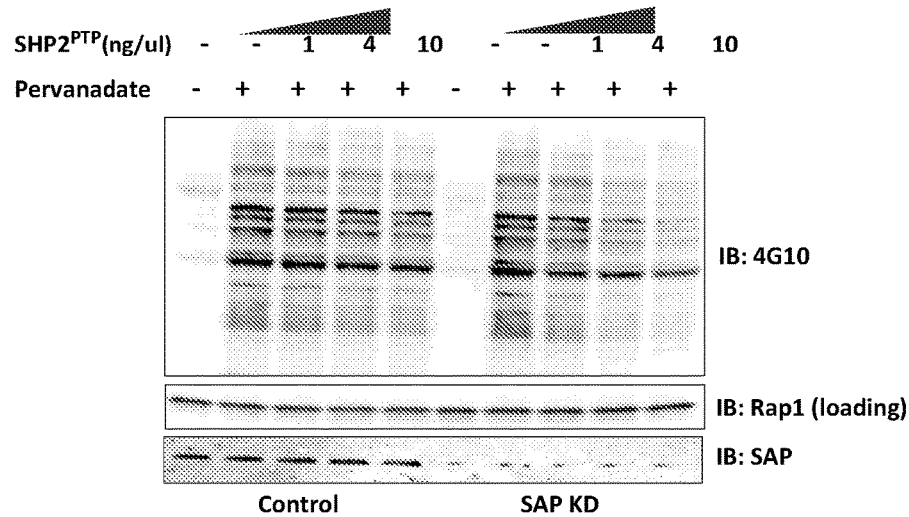
Figure 4:
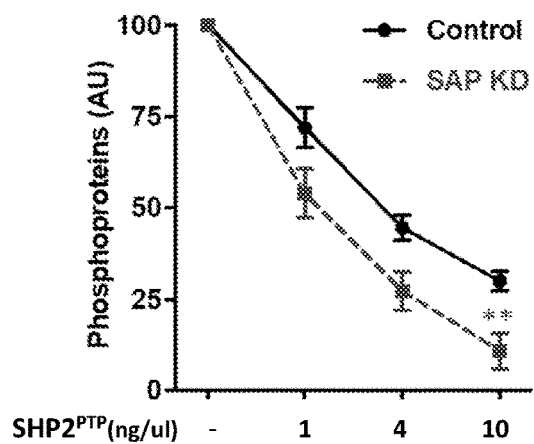
Figure 4:
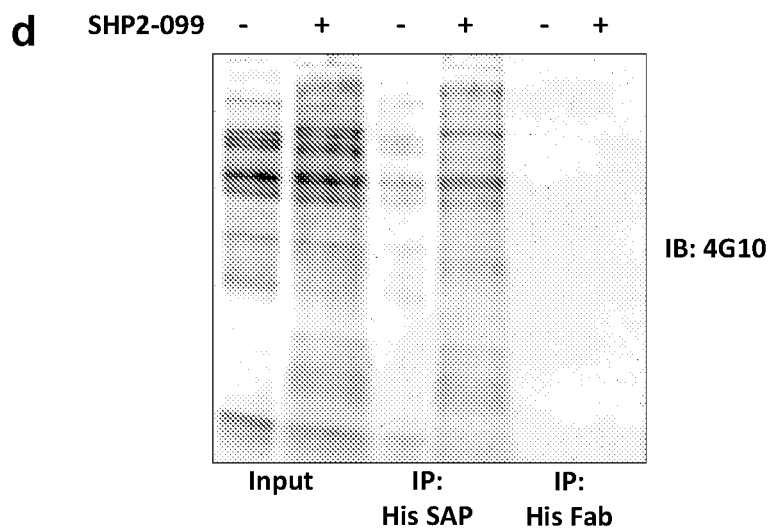
Figure 4:
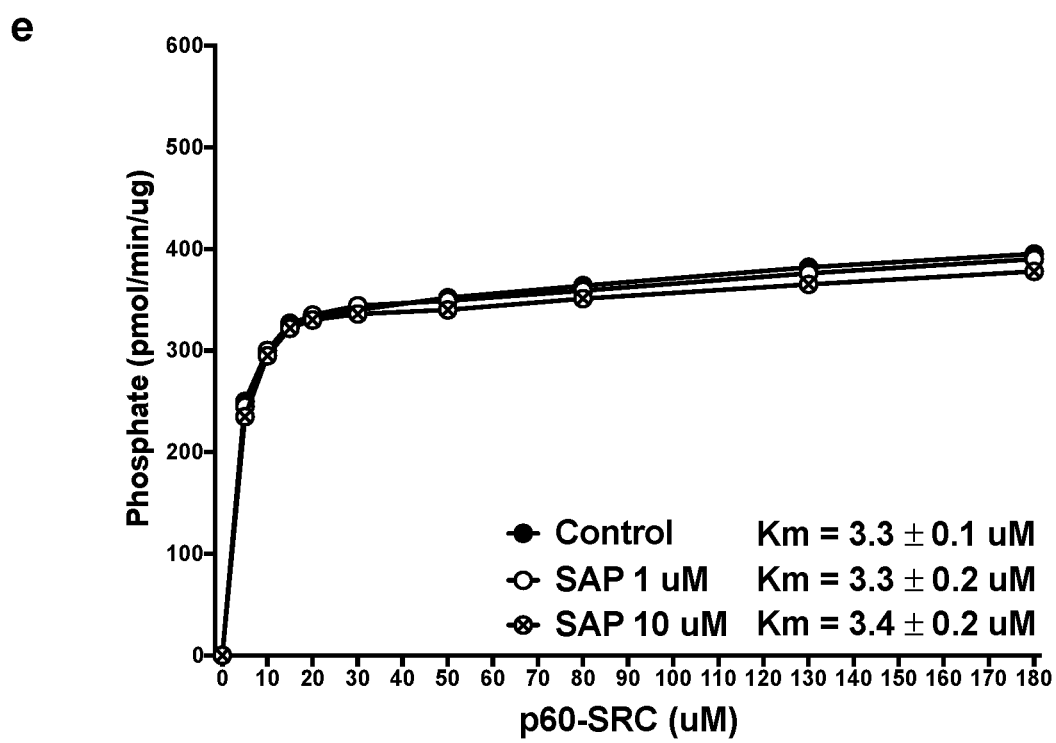
Figure 4:
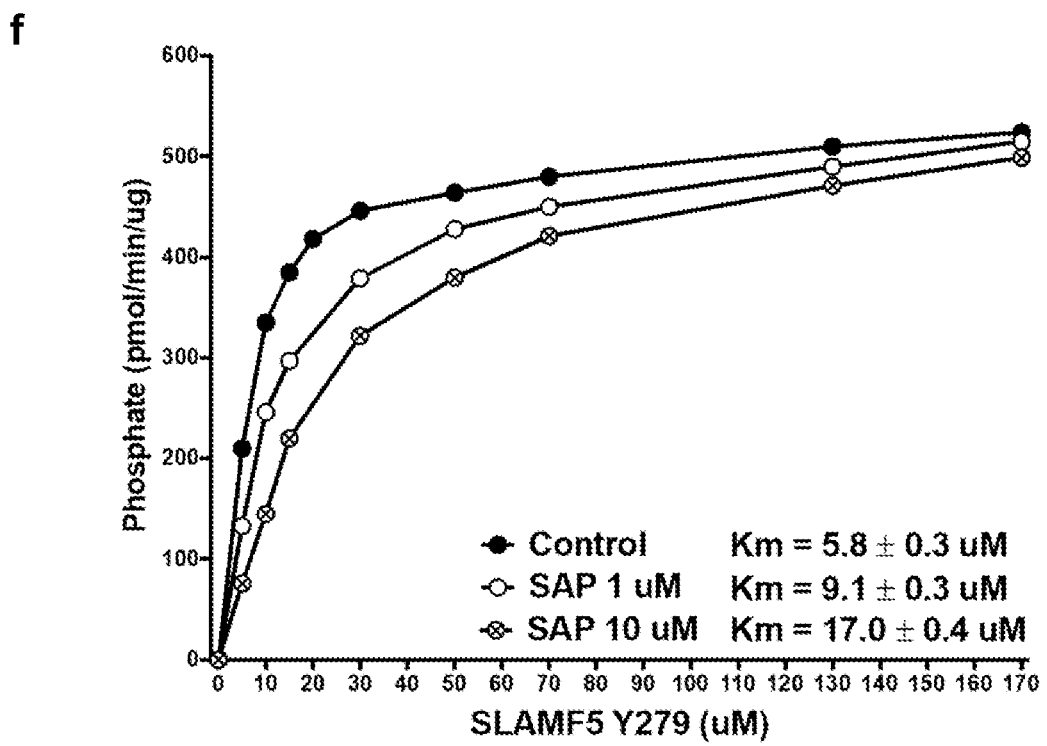
Figure 4:
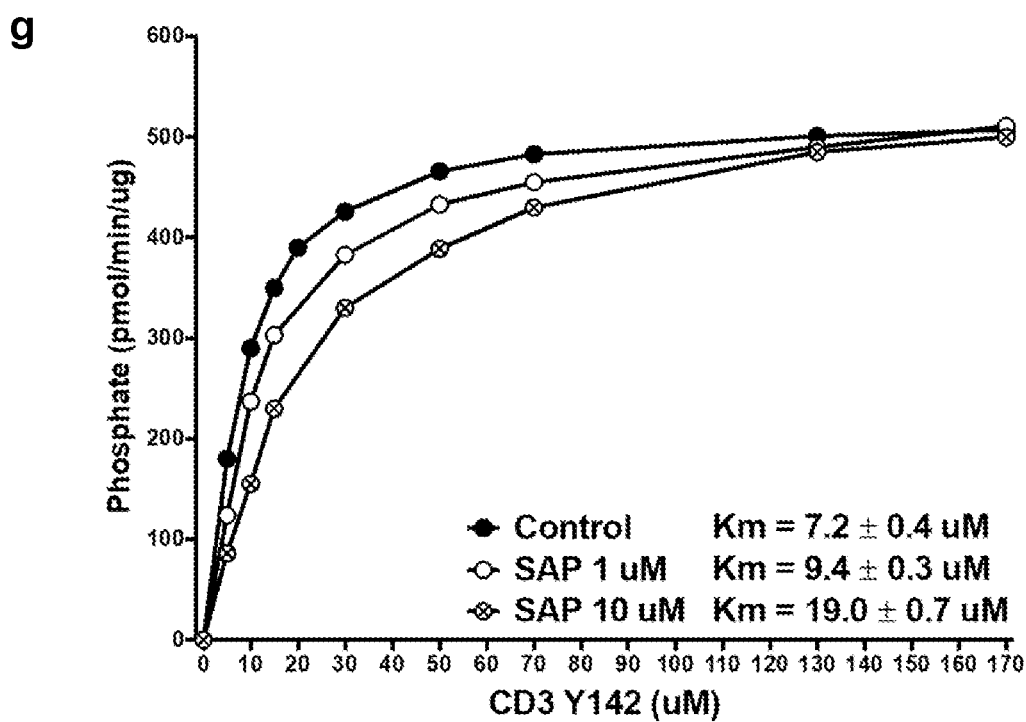
Figure 4:
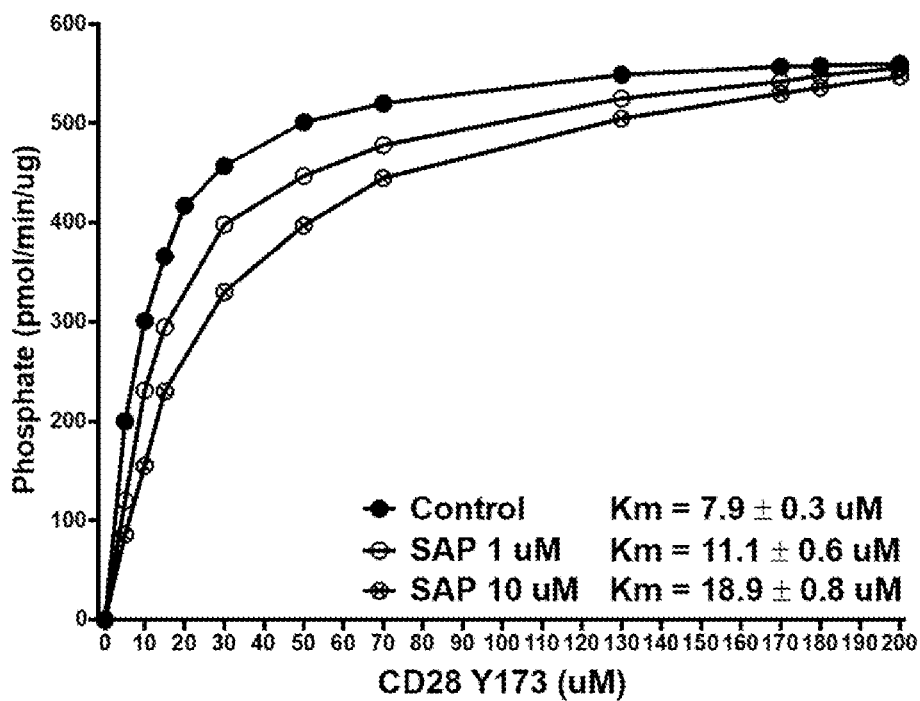
Figure 4:
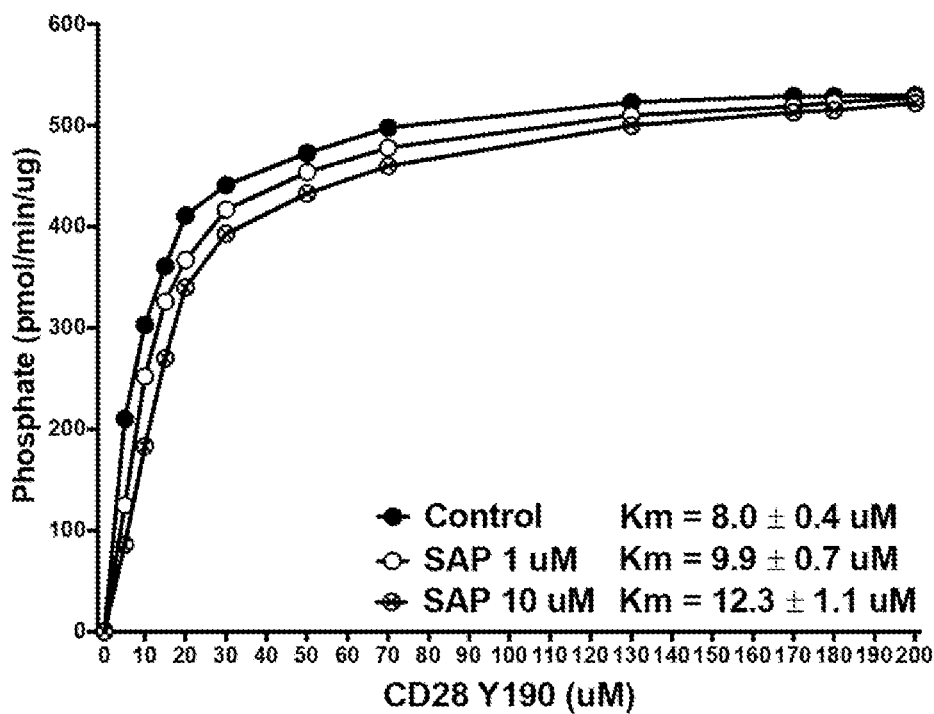
Figure 4:
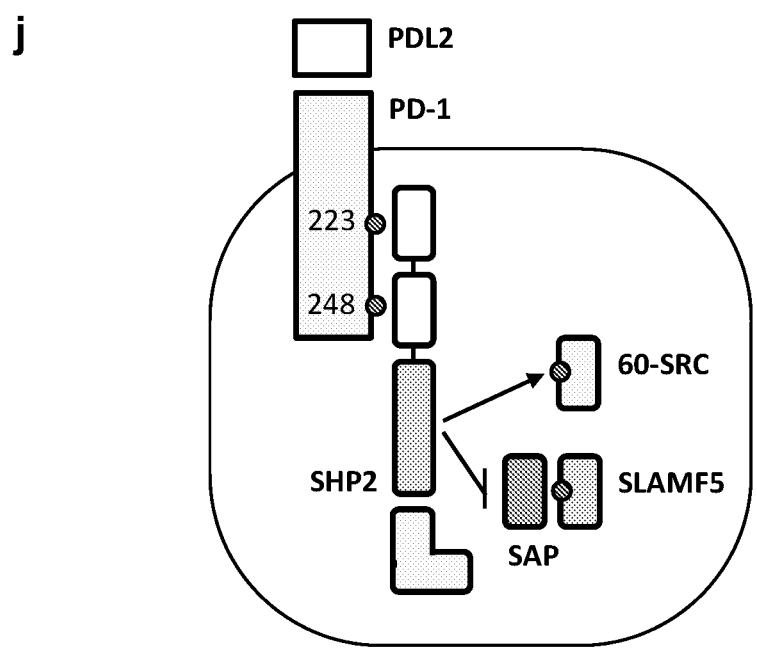
Figure 11:
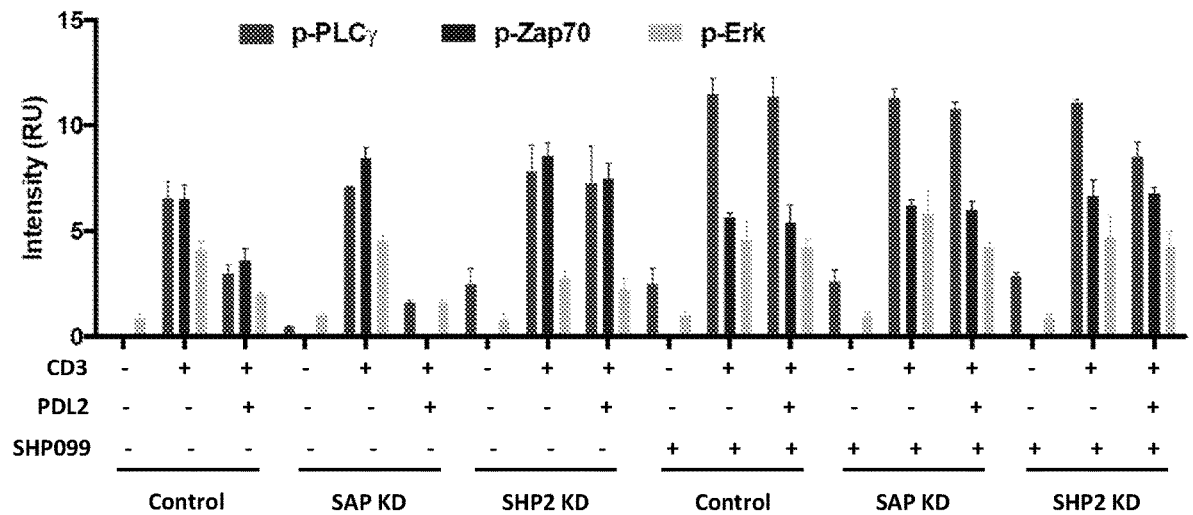
FIG. 11. Densitometry values of data shown in FIG. 4$a$. The bars from left to right for each set are: p-PLCγ, p-Zap70, p-Erk.
Figure 12:
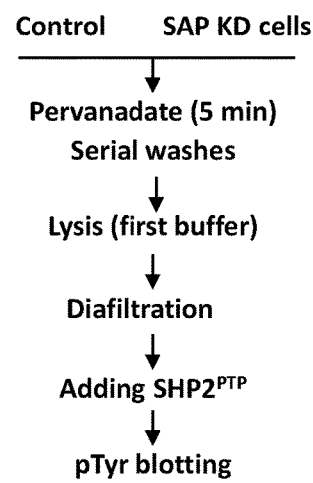
FIG. 12. Diagram describing the workflow of the modified phosphatase activity assay. Jurkat T cells, transfected with siRNA for SAP (SAP KD) and non-targeting control (Control), were treated with pervanadate to induce maximal phosphorylation, followed by five serial washes, lysis and diafiltration in order to remove the drug and to exchange the buffer to a phosphatase-compatible buffer. SHP2PTP (GST tagged SHP2 catalytic domain) was then added to the cell lysates for 1 hour, at the indicated concentrations, followed by immunoblotting with anti-phosphotyrosine antibody (4G10).

We investigated if SAP modulates signaling downstream of PD-1. Knocking down SAP in Jurkat T cells further enhanced the ability of PD-1 ligation (with PDL2) to inhibit the phosphorylation of ERK, PLCγ and ZAP70 in CD3-stimulated T cells (FIG. 4a; left panel). Moreover, when SAP-deficient T cells were treated with SHP099, an allosteric specific inhibitor of SHP2, PD-1's ability to inhibit the phosphorylation of ERK, PLCγ and ZAP70 was abrogated (FIG. 4a; right panel and quantified in FIG. 11). To test if SAP inhibits dephosphorylation of SHP2 substrates, we used a modified phosphatase assay that was based on the in vitro substrate-trapping method (Mercan et al., *Current protocols in molecular biology Chapter* 18:Unit 18 16) (FIG. 12 and FIG. 4b). As shown, a decrease in the levels of the phosphorylated proteins were recorded with increasing concentration of SHP2$^{PTP}$ (FIGS. 4b and 4c). Most importantly, there was an enhanced reduction of total phosphorylation in the SAP-deficient cells (FIGS. 4b and 4c), implying that SAP inhibits SHP2 specific activity.

Because SAP inhibits PD-1 signaling (FIG. 4a), but does not interfere with SHP2 binding to PD-1 (FIGS. 3e and 3f), we considered two alternative mechanisms. First, SAP could bind SHP2 and directly block the SHP2 catalytic site, or alternatively, SAP might not bind to SHP2, but rather could bind to its substrates and thereby block the interaction between SHP2 and its enzymatic substrates. In support of the latter model, we used SHP099 to block SHP2 activity in Jurkat T cells, followed by affinity purification with His-tagged SAP. As expected (FIG. 4d), SHP099 treatment resulted in increase in the levels of select tyrosine phosphorylated proteins (detected by 4G10 antibody). The fact that these SHP2 phosphorylated targets were also affinity purified by His-tagged SAP, indicates that SAP physically interacts with several SHP2 substrates (FIG. 4d). To test the effect of SAP on SHP2 mediated dephosphorylation events, we measured SHP2-mediated dephosphorylation of p60-SRC Y416 (FIG. 4e), SLAMF5 Y279 (FIG. 4f), and CD3 Y142 (FIG. 4g) phosphotyrosyl peptides by Malachite Green assays. For these three substrates, and in the absence of SAP, we observed a conventional Michaelis-Menten kinetics. However, when we included SAP in the assay, we observed that SHP2 mediated dephosphorylation was inhibited only when the SHP2 substrate was a known SAP interactor (CD3 and SLAMF5 but not p60-SRC) (FIGS. 4f and 4g). Consistent with a competitive mechanism of inhibition, Km values increased 2-3-fold in the presence of SAP when phosphorylated SLAMF5 and CD3 peptides were used as substrates, but not when p60-SRC peptide was used, whereas Vmax values were unaffected for all three phosphotyrosyl peptides. The cytoplasmic tail of CD28 was reported to be a significant target for SHP2 downstream of PD-1 (Hui et al., Science 355(6332):1428-1433). To assess if SAP inhibits the dephosphorylation of the tail of CD28, we tested recombinant CD28 Y173, the binding site of lipid kinase phosphatidylinositol 3-kinase (PI3K), and recombinant CD28 Y190, the LCK binding motif. Although both sites were targeted by the catalytic domain of SHP2 (FIGS. 4h and 4i), SAP predominantly inhibited dephosphorylation of CD28 Y173 over CD28 Y190. The Km values for CD28 Y173 were similar to those of CD3 Y142, but lower than the values for CD28 Y190. Overall, SAP interacts with PD-1 and SHP2 indirectly, and inhibits their activity by shielding substrates of SHP2 from its phosphatase activity (FIG. 4j).

SAP Inhibits PD-1 Functions.

Figure 5:
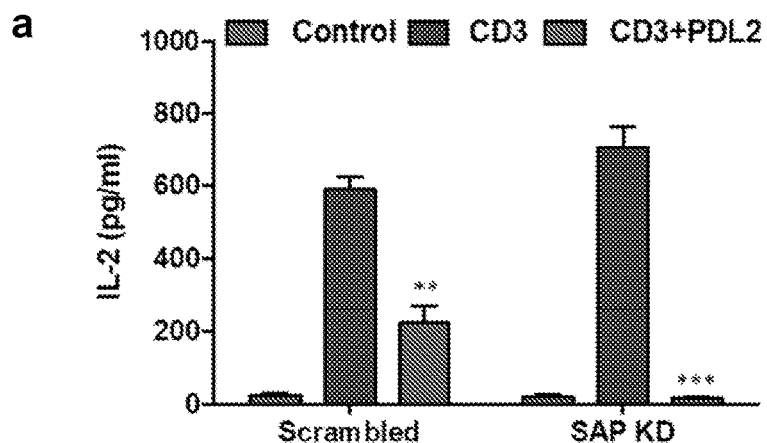
FIG. 5. SAP inhibits PD-functions. (a) Freshly isolated human $CD3^+$ T cells were transfected with non-targeting control siRNA or siRNA targeting SAP or (b-d) with a plasmid directing expression of different levels of SAP-GFP (low SAP for 0.4 ug DNA/plate and high SAP for 4 ug DNA/plate), or control null plasmid. After 24 hours, the cells were stimulated with magnetic beads coated with anti-CD3, or anti-CD3+PDL2 for additional 24 hours. At this time, cells were tested for GFP and for CD69 expression by FACS analysis (b and d), and media was collected for IL-2 (a, c) measurements (ELISA). (e, f) Jurkat T cells, stably transfected with shRNA targeting SAP (KD; knockdown) or a plasmid directing expression of SAP (OE; overexpression), were stimulated as indicated and media was collected for IFN-γ, while cells were subjected to an adhesion assay using fibronectin coated wells. Percentage of adhesion was calculated based on input fluorescence. (g) Freshly isolated human $CD3^+$ T cells from healthy controls or from XLP patients were stimulated with magnetic beads coated as indicated for 48 hours. Media was harvested, and IL-2 levels were measured with ELISA. (h) Freshly isolated human CD3+ T cells from healthy controls or from XLP patients were stimulated with magnetic beads coated as indicated and cell proliferation was monitored using the MTS assay. Values are expressed as increase in OD compared with day 0. (i) Freshly isolated mouse CD3+ T cells from WT controls or from SAP-deficient mice were stimulated with magnetic beads coated as indicated for 48 hours. Media was harvested, and IL-2 levels were measured with ELISA. (j) Freshly isolated mouse CD3+ T cells from WT controls or from SAP-deficient mice were stimulated with magnetic beads coated as indicated and cell proliferation was monitored using the MTS assay. Values are expressed as increase in OD compared with day 0. Data are represented as mean±SEM. *,  or * represent significant differences, between the denoted condition and the anti-CD3 treated cells in a and c-f or between the denoted group and the anti-CD3+28 treated cells in g-j; * P<0.05, ** P<0.01, * ** P<0.001, n=3, unpaired t test. For FIGS. 5$a$, 5$c$, 5$d$, 5$e$, 5$f$, 5$g$ and 5$i$, the bars from left to right for each set are: Control, CD3, and CD3+PDL2
Figure 5:
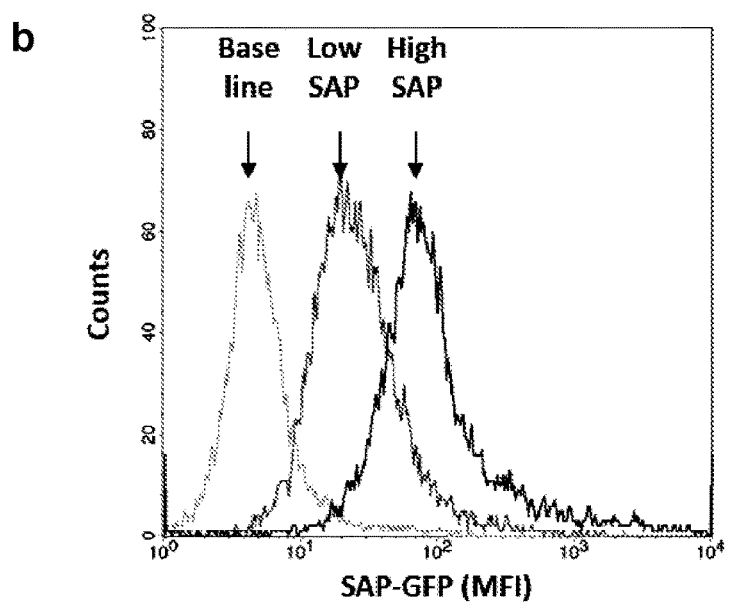
Figure 5:
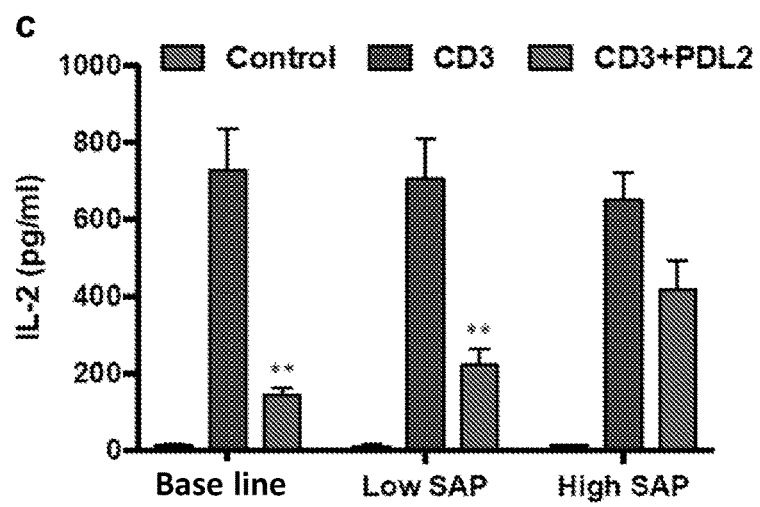
Figure 5:
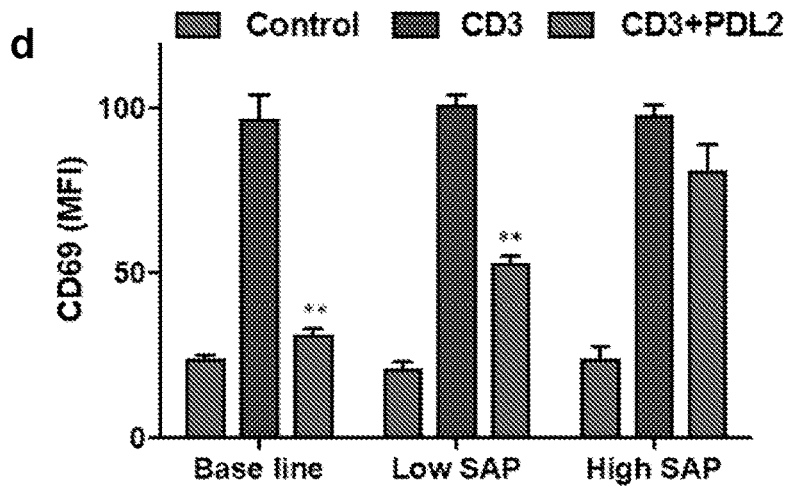
Figure 5:
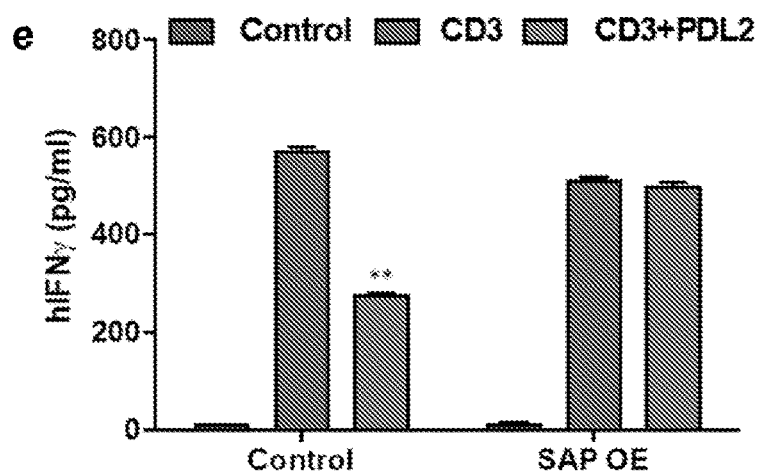
Figure 5:
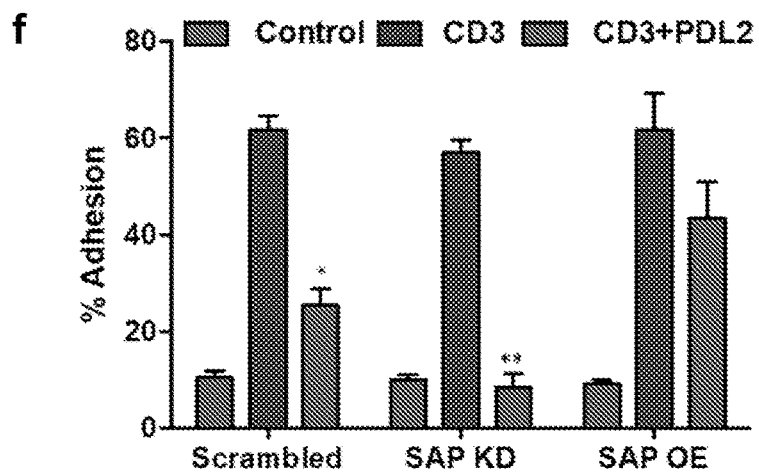
Figure 5:
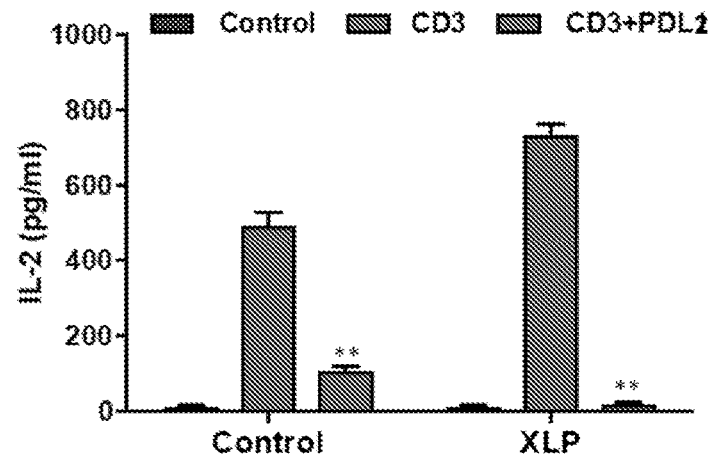
Figure 5:
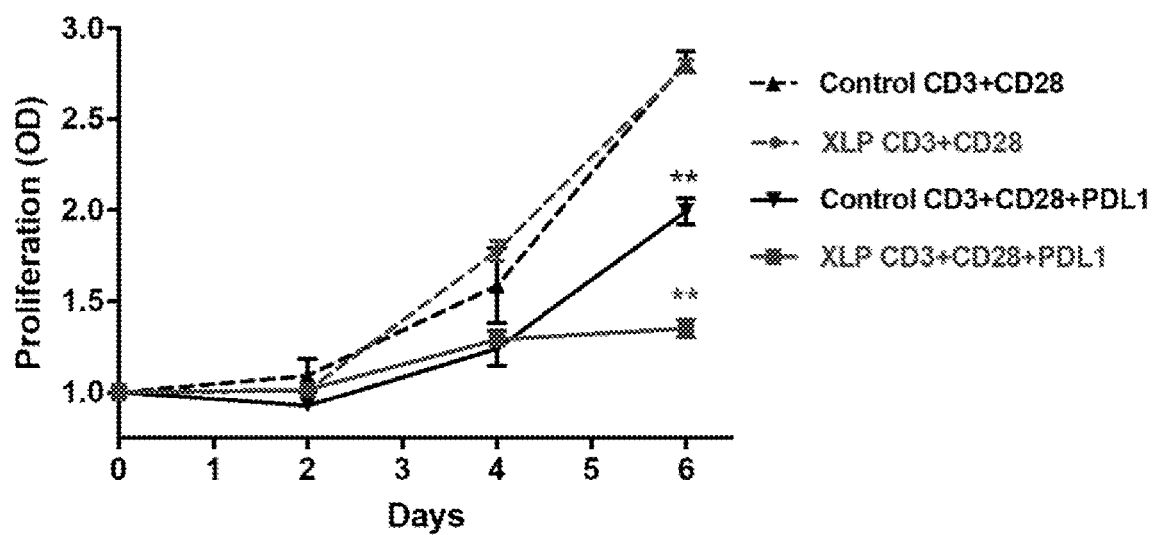
Figure 5:
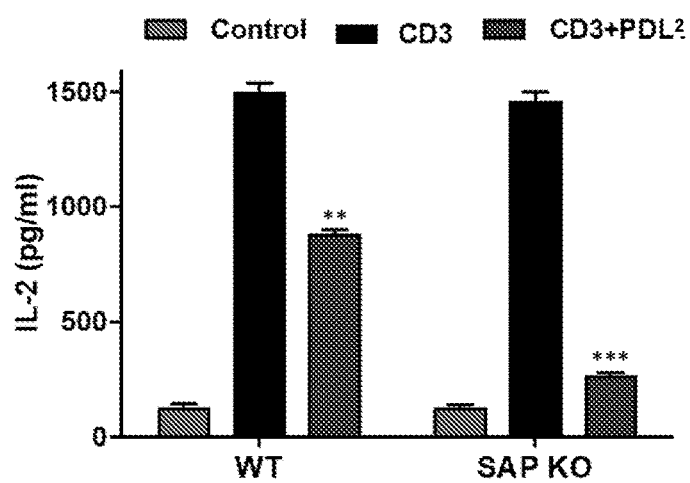
Figure 5:
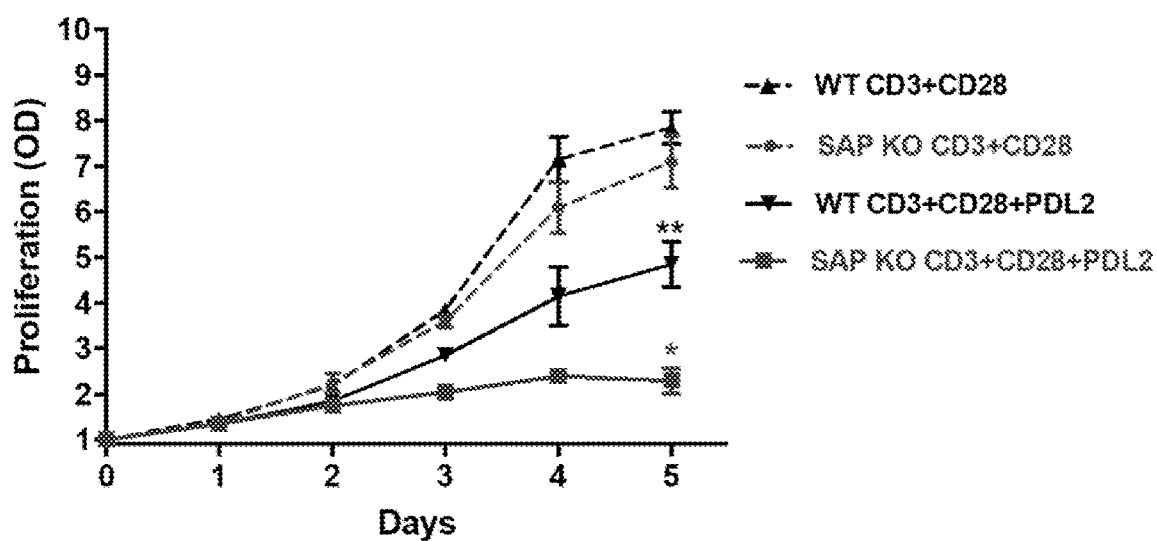
Figure 13:
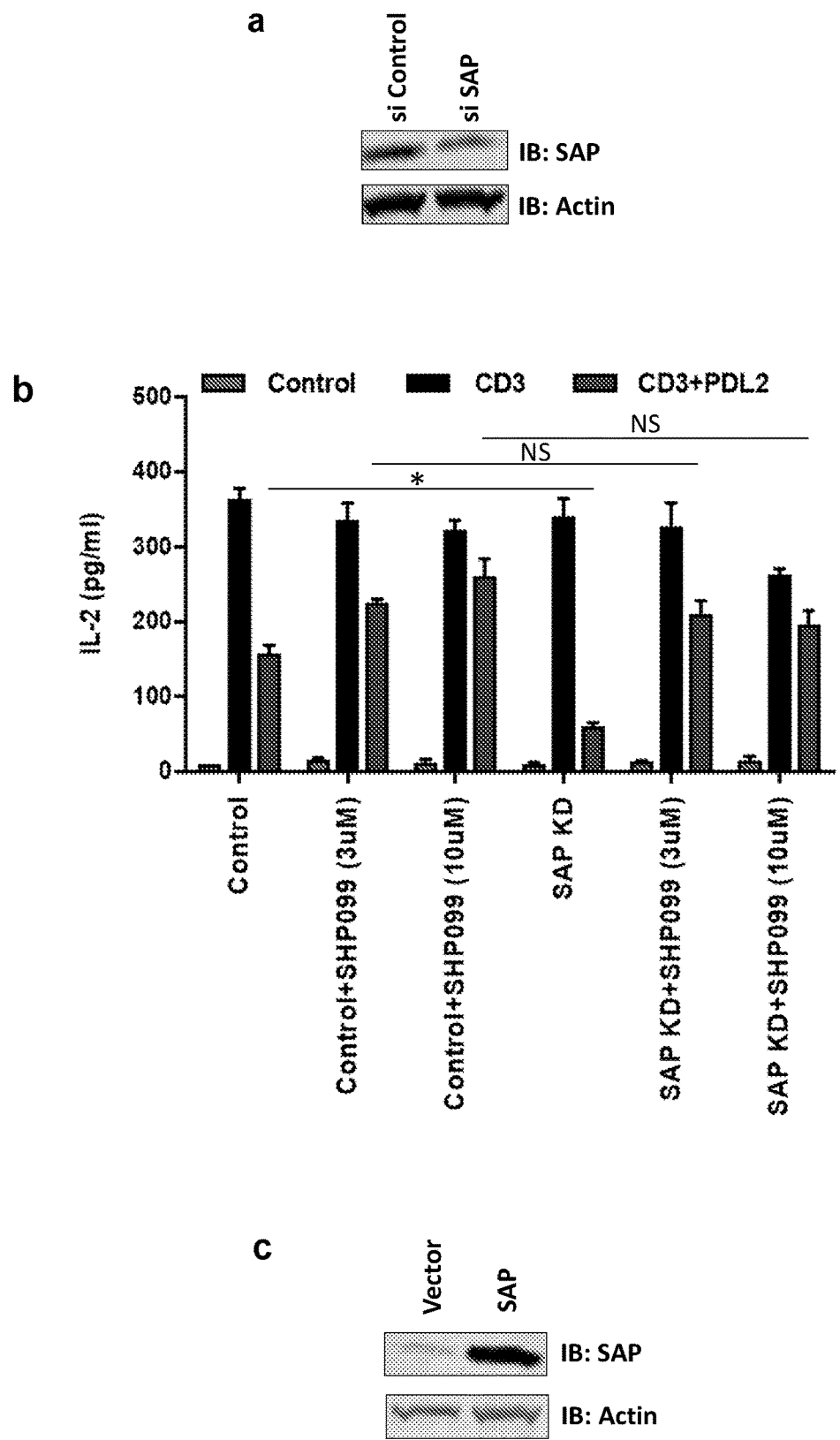
FIG. 13. (a) Jurkat T cells were transfected with non-targeting siRNA control and siRNA to SAP, followed by immunoblot analysis. (b) Freshly isolated human CD3+ T cells were transfected with non-targeting control siRNA (Control) or siRNA targeting SAP (SAP KD), treated with SHP099 (SIP2 inhibitor) at the indicated concentrations, followed by stimulation with magnetic beads coated with anti-CD3, or anti-CD3+PDL2 for additional 24 hours. Media was harvested and IL-2 levels were measured (ELISA). * P<0.05, NS not significant, n=3, unpaired t test. (c) control vector or SAP-expressing vector for 48 hours and samples were analyzed for SAP expression by immunoblotting. (d) Cell expressing SAP were stimulated overnight and CD69 expression levels were recorded by FACS. (e) T cells from XLP patients and healthy controls were tested for PD-1 expression by FACS analysis. For FIG. 7$b$ 13$b$, the bars from left to right for each set are: Control, CD3, and CD3+PDL2.
Figure 13:
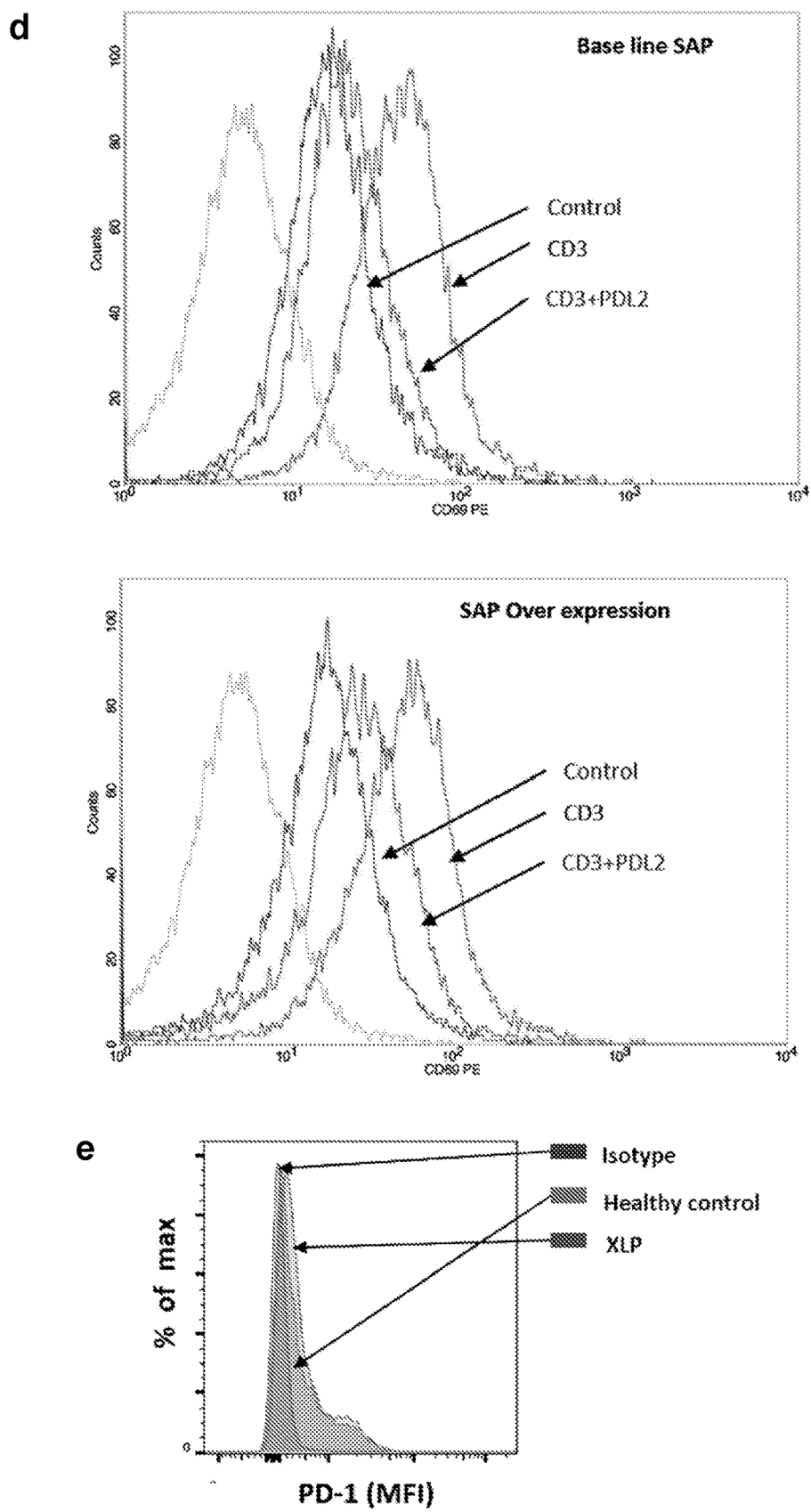

Functionally, knocking down SAP in primary human T cells using siRNA (FIG. 13a) further enhanced the ability of PD-1 ligation (with PDL2) to inhibit IL-2 secretion in anti-CD3-stimulated T cells (FIG. 5a), and similar to its effect on PD-1 signaling, treatment with SHP099 resulted in abrogation of PD-'s ability to inhibit IL-2 secretion (FIG. 13b). By contrast, overexpression of SAP-GFP (FIG. 13c and FIG. 5b) abrogated the ability of PD-1 to inhibit anti-CD3-induced IL-2 secretion (FIG. 5c), CD69 up regulation (FIG. 5d and FIG. 13d), IFN-γ release (FIG. 5e), and T cell adhesion to fibronectin-coated wells (FIG. 5f). Thus, SAP appears to be a negative regulator of PD-1 signaling and function in T cells.

X-linked lymphoproliferative disease (XLP) is a genetic disease in which the SH2D1A gene (which encodes SAP) is mutated, leading to either an absent or dysfunctional protein. XLP patients are immunodeficient and commonly present with dysregulated cellular responses to Epstein-Barr virus infection, which results in excessive lymphoproliferation or hemophagocytic lymphohistiocytosis. To further validate the contribution of SAP to PD-1 signaling, we isolated peripheral T cells from patients with XLP to study the ability of anti-CD3 and +PDL2-Fc coated beads to modulate cytokine secretion. Compared with healthy control T cells, PD-1 ligation in XLP cells resulted in more profound reduction of IL-2 secretion (FIG. 5g). PD-1 ligation had also a more pronounced inhibitory effect on cellular proliferation in XLP cells in comparison to cells from healthy controls downstream of PD-1 (FIG. 5h), strongly suggesting that SAP is a negative regulator of PD-1 functions. Importantly, PD-1 expression levels were maintained at equivalent levels in XLP patients and controls (FIG. 13e). Similar to XLP patients, T lymphocytes from SAP-deficient mice had an increased response to PD-1 activation as demonstrated by a further reduction of IL-2 secretion and cellular proliferation (FIGS. 5i and 5j).

SAP Expression Levels Inversely Correlate to PD-1 Signaling in Purified T Cell Subsets.

Figure 6:
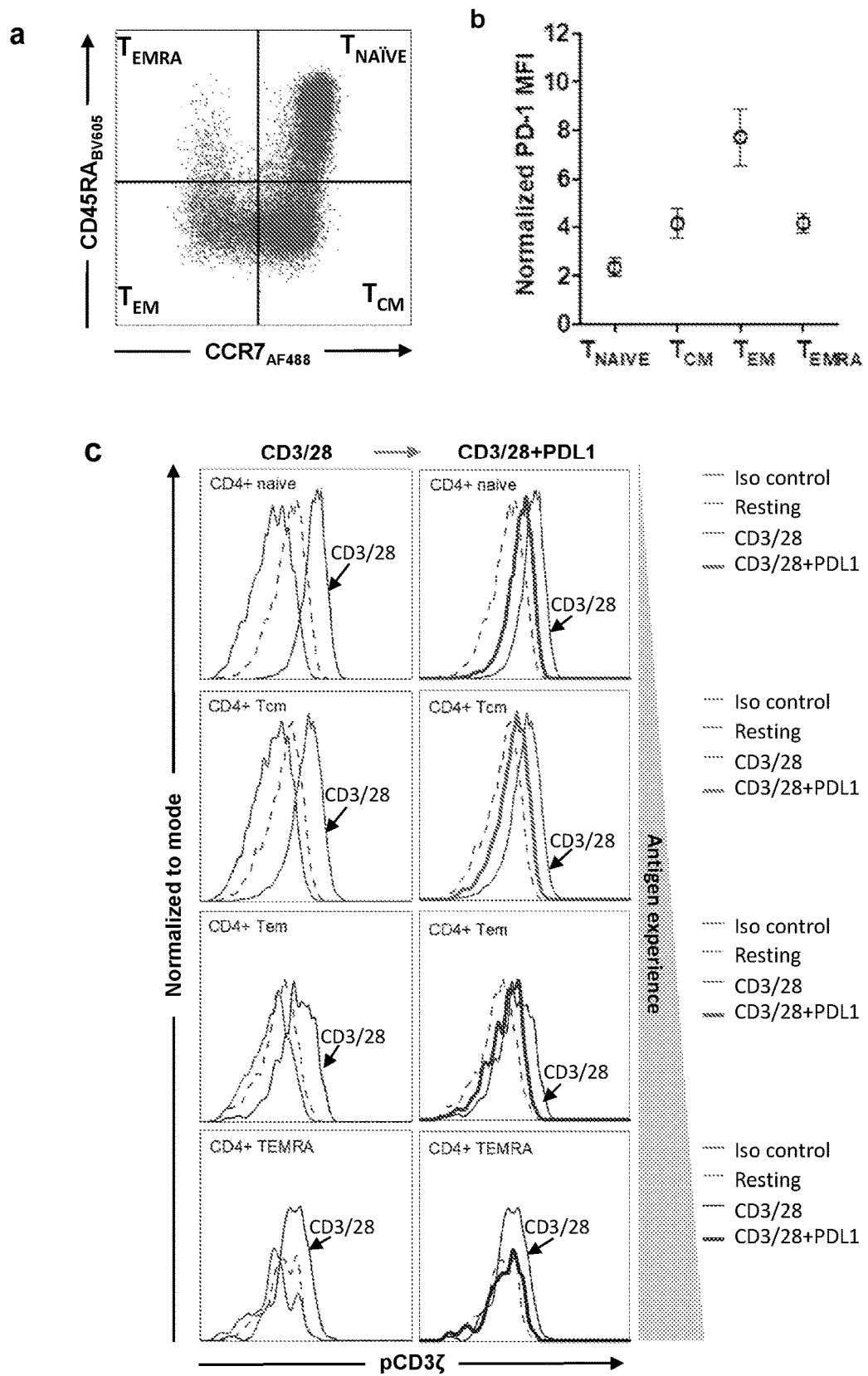
FIG. 6. SAP expression levels inversely correlate to PD-1 signaling in purified T cell subsets. (a) Expression of CD45RA and CCR7 by human CD4+ T cells in blood defines four subsets corresponding to $T_{NAIVE}$ (CD45RA+CCR7+, top right quadrant), terminal effector ($T_{EMRA}$; CD45RA+ CCR7−, top left quadrant), central memory ($T_{CM}$; CD45RA− CCR7+, bottom right quadrant), and effector memory ($T_{EM}$; CD45RA−CCR7−, bottom left quadrant) cells. Results shown are from one donor, representative of five donors. (b) Expression of PD-1 in the different T cell subsets expressed as the median of fluorescence intensity (MFI). (c) Representative histograms of pCD3ζ (staining: grey histogram (Iso control); colored histogram (crosslinked with anti-CD3/ CD28 antibodies); dashed line (resting cells); thick colored line (crosslinked with anti-CD3/28 antibodies in the presence of PDL1). (d) CD3ζ dephosphorylation. The MFI of pCD3ζ for each subset was normalized to the MFI of anti-mouse IgG antibody alone. The proportion of CD3ζ dephosphorylation was calculated as percent change for each subset relative to the crosslinked sample (% CD3ζ dephosphorylation=100−((crosslinked+PDL1/cross-linked) *100)). (e) Expression of SAP in the different T cell subsets expressed as the median of fluorescence intensity (MFI). (f) Linear regression of the percentage of CD3ζ dephosphorylation is plotted against the linear regression of SAP expression in the different subsets. Data are represented as mean±SEM.* P<0.05, n=3, unpaired t test.
Figure 6:
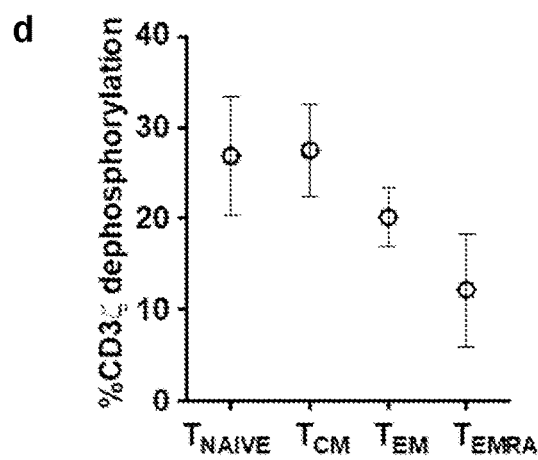
Figure 6:
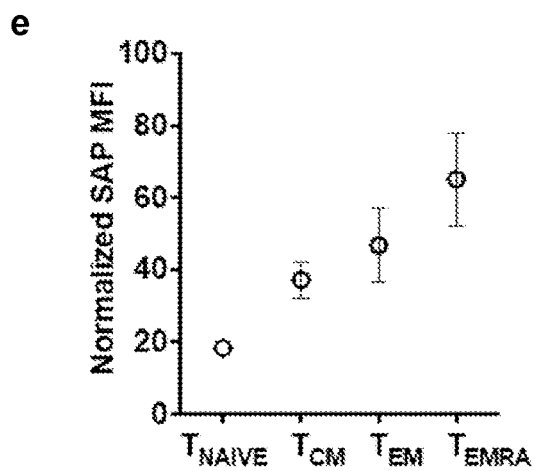
Figure 6:
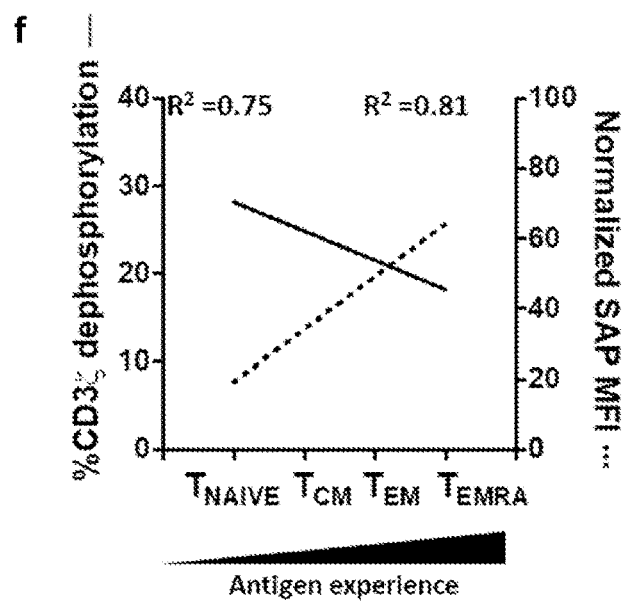
Figure 14:
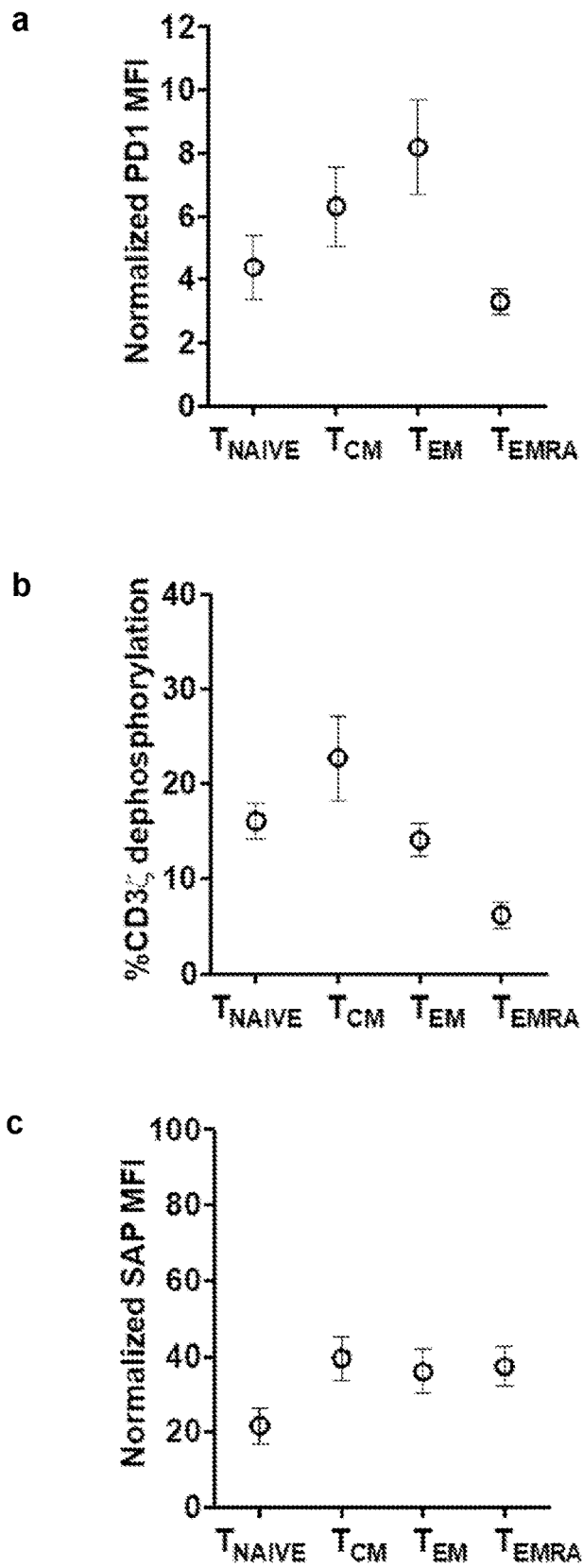
FIG. 14. SAP is inversely correlated with PD-1 signaling in CD8 T cell subsets. (a) Expression of PD-1 in the different T cell subsets expressed as the median of fluorescence intensity (MFI). (b) CD3ζ dephosphorylation. The MFI of pCD3ζ for each subset was normalized to the MFI of anti-mouse IgG antibody alone. The proportion of CD3ζ dephosphorylation was calculated bas percent change for each subset relative to the crosslinked sample (% CD3ζ dephosphorylation=(100−((crosslinked+PDL1/crosslinked) *100))). (c) SAP expression in the different T cell subsets expressed as the median of fluorescence intensity (MFI). Data are represented as mean SEM.
Figure 15:
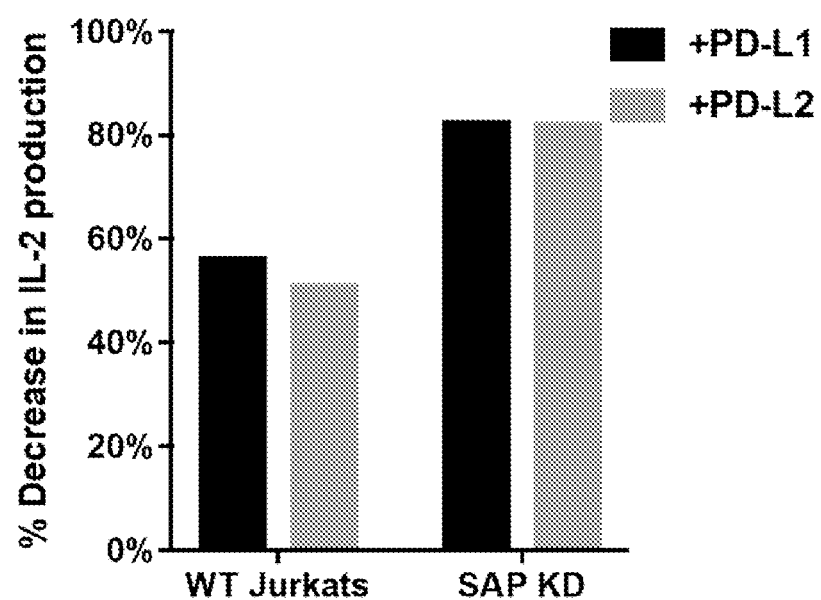
FIG. 15. Wild type (WT) Jurkat T cells, or Jurkat T cells stably knocked down for SAP (SAP KD) were stimulated with anti-CD3 or with antiCD3+PDL1/2 and for 24 hours, and IL-2 levels were measured by flow using intracellular staining. Percent reduction (from baseline, i.e., anti-CD3) of IL-2 levels is shown.

To test whether different expression levels of SAP affect PD-1 function in a physiologic setting, we first separated CD4$^+$ T cells into the following subsets (based on different stages of antigen experience): naïve T cells ($T_{NAIVE}$), central memory T cells ($T_{CM}$), effector memory T cells ($T_{EM}$) and terminally differentiated T cells ($T_{EMRA}$)(FIG. 6a). As expected, PD-1 expression levels differed between these subsets (FIG. 6b and FIG. 14 for CD8$^+$ T cells). To analyze PD-1 signaling, we measured phosphorylation levels of tyrosine 142 of the (chain of the TCR complex (pCD3ζ), as the most proximal phosphorylation event in the TCR signaling cascade, which is also dephosphorylated upon PD-1 engagement. As expected, pCD3ζ levels increased upon crosslinking with anti-CD3/28 antibodies (FIG. 6c; left column), and decreased when PDL1 was engaged concomitantly (FIG. 6c; right column). Interestingly, increased PD-1 expression levels (FIG. 6b) failed to correlate with the effects of PD-1 ligation on TCR signaling in different T cell subsets, as measured by pCD3ζ levels de (FIG. 6d). By contrast, SAP expression levels positively correlated with antigen experience (FIG. 6e), and inversely correlated with the degree of CD3ζ dephosphorylation (FIG. 6f), suggesting a role for SAP in inhibiting PD-1 function in T cell subsets. To further support this hypothesis, SAP knockdown in Jurkat T cells resulted in greater reduction of IL-2 levels downstream of PD-1, measured by intracellular staining (FIG. 15). Collectively, these results suggest that SAP acts as a negative regulator downstream of PD-1 signaling.

In this work, we utilized an affinity purification-based approach, using the GST-tagged PD-1 cytoplasmic tail as a bait, coupled with MS analysis, to identify intracellular binders. Focusing on tyrosine-specific interactors, we used relative label-free quantitative analysis to discover candidates that preferentially interacted with the PD-1 WT and not with the phosphodeficient version. Because ITIMs or ITSMs usually recruit adaptor proteins that have SH2 domains, we focused our attention on proteins that were enriched in the PD-1 WT affinity purification and that also contain at least one SH2 domain (uniprot.org). Further limiting our consideration to immune related proteins narrowed our list to only three candidates: SHP2, ITK and SAP). Interestingly, SHP1 was not affinity-purified by any of the C-terminal tails. While SHP2 is a known binding partner of PD-1, SAP has never been demonstrated to interact with this receptor. As SAP is known to interact with the ITSMs of the SLAM family receptors, other investigators attempted, although unsuccessfully, to record an association between PD-1 and SAP using 293T cells (Chemnitz et al., Journal of immunology 173(2):945-954). In our hands, overexpression of SAP impaired PD-1 inhibitory function by obstructing SHP2 phosphatase activity. This was related to a shielding effect of SAP, whereby SAP protects substrates of SHP2 from its phosphatase activity. The formation of an inhibitory complex that includes SAP, and perhaps additional proteins, to modulate SHP2 activity through an alternative mechanism cannot be excluded.

Our finding that SAP protects CD28 from dephosphorylation by SHP2 further support the important role of SAP in PD-1 signaling and provide an additional layer of evidence that many SHP2 sites that overlap with SAP binding may actually be shielded from PD-1 signaling, leaving those not shielded by SAP as major functional targets. There are two functional phosphosites in the tail of CD28. The first motif contains HSDY(p)MNM sequence (CD28 Y173). This motif undergoes tyrosine phosphorylation following the engagement of CD28 and serves as a binding site for the SH2 domain of p85, the regulatory subunit of PI3K. The methionine residue at the +3 position confers specificity for p85 binding, while the asparagine at the +2 position confers additional specificity for the SH2 domain of GRB2 and GADS. A second more distal motif containing YQPY(p) APP (CD28 Y190) serves as a potential docking site for other effector molecules such as filamin-A, LCK and FYN. We found that SAP preferentially shields the first motif, and this might result from the serine at −2 position of CD28 Y173, which is considered part of the binding motif of SAP Immunodeficiency and lymphoproliferative disease coexist in XLP patients (Filipovich et al., *Blood* 116(18):3398-3408). Similarly, SHP2 is implicated in opposite signaling pathways, as it is involved in mediating lymphoproliferation, being an inducer of the RAS pathway (Zhang et al., *Molecular cell* 13(3):341-355), as well as an inhibitor of lymphoproliferation and other lymphocyte functions as a mediator of the PD-1 pathway. Hence, the function of SAP as an inhibitor of SHP2 can explain the pathophysiology of XLP and also points towards SHP2 inhibitors as a possible therapy.

We observed a partial reduction in SHP2 binding to PD-1 when the ITIM was mutated. We also found that the enzymatic activity of SHP2 was reduced when either the ITIM or the ITSM were mutated, implying that the ITIM is required for optimal binding of SHP2 to PD-1, SHP2 enzymatic activity, and overall PD-1 function. We find that while both ITIM and ITSM of PD-1 were involved in SHP2 recruitment, a mutation in the ITIM alone completely abolishes SHP2 activity and PD-1 function. This discrepancy can be explained by the two-step activation model, where the first step involves recruitment to the ITSM without activation (because of the auto-inhibited conformation of SHP2), and only when there is binding of the second SH2 to the ITIM (second step), SHP2 becomes active (FIG. 2f).

Our findings indicate that inter-patient differences in SAP levels might be of relevance to anti-PD1 response. Further, the newly discovered binding partners of the PD-1 cytoplasmic tail, presented in this study, hold great potential as novel therapeutic targets.

Materials and Methods

Additional information regarding the materials and methods is provided in the supplemental material.

Transfection, and Stimulation.

Constructs were introduced into the cells by nucleofection (Lonza) with an efficiency of 50 to 70%. Cells were stimulated at a 1:3 ratio with magnetic beads ($3 \times 10^6$ beads per well) (Invitrogen) conjugated with anti-CD3 (UCHT1; R&D) and IgG1 (R&D) or with anti-CD3 and PD-L2-IgG1 (R&D).

Recombinant Proteins.

Recombinant peptides were synthesized by GenScript.

DNA Constructs.

pMSCV-PD-1-YFP was a gift from James Allison (MD Anderson). mCherry-hLC3B-pcDNA3.1 was a gift from David Rubinsztein (Addgene #40827) (Traffic 2008; 9:574-87). pMSCV-SHP2-flag and pMSCV-null were previously described (Mohi M G, et al. (2005) *Cancer cell* 7(2):179-191).

Generating Stable Knockdown Jurkat T Cells.

SAP was stably knocked down in Jurkat T cells by RNA interference using Mission shRNA plasmids (Sigma).

siRNA for Knockdown in Primary Human T-Cells.

SMARTpool ON-TARGETplus SH2D1A (SAP), SHP2, and non-targeting control siRNA (Dharmacon) were used according to the manufacturer's instruction.

Cytokine Analysis.

Human and mouse IL-2 and IFN-γ ELISA kits (BioLegend) were used according to the manufacturer's protocols.

Cell Proliferation Assay.

Cell proliferation assay was performed using tetrazolium compound based CellTiter 96® AQueous One Solution Cell Proliferation (MTS) assay (Promega).

Immunoprecipitation and Affinity Enrichment.

Cell lysates were mixed with anti-GFP monoclonal antibody coupled to agarose beads to enrich GFP tagged proteins according to the manufacturer's protocols. Pull down lysates were separated by tris-glycine PAGE and transferred to nitrocellulose filters and visualized as described (Azoulay-Alfaguter et al., *The Journal of allergy and clinical immunology* 135(2):564-567). Bacterial expression vectors were used to transform competent BL21 *E. coli* cells. Recombinant protein immobilization on glutathione sepharose beads (Thermo Scientific), binding assays and analyses of bound proteins were conducted as described (Li et al. (2004), *The EMBO journal* 23(5):1112-1122).

Phosphatase Activity.

To determine kinetic parameters, a fixed amount of purified GST-WT SHP2 catalytic domain was incubated with variable concentrations of substrates in (GenScript) in PTP assay buffer (Phosphatase assay kit; Upstate 17-313). Phosphatase release was quantified by adding Malachite Green (Malachite Green phosphatase detection kit; R&D DY996).

Flow Cytometry. T cells were studied using FACSCalibur (BD) and LSR II flow cytometer (BD) and analyzed using FlowJo software.

Static Adhesion Assay.

Static T cell adhesion to fibronectin-coated plates was performed as reported (Strazza et al., *Journal of visualized experiments: JoVE* (88)).

Mass Spectrometry (LC-MS/MS).

The samples were digested in gel and analyzed on LCMS as in Drummond et al., (*Scientific reports* 5:15456) with modifications as described in the supplemental material. The MS/MS spectra were searched against the UniProt Human reference proteome database (downloaded 2-25-16)(UniProt C (2015) *Nucleic acids research* 43(Database issue):D204-212), with wild type and phosphor impaired GST-PD1 sequences inserted into the database, using Sequest within Proteome Discoverer. Database queries to sort for SH2 containing proteins and immune-related proteins are described in detail in the supplemental material.

XLP Patients and Healthy Controls.

The study was approved by the Institutional Review Board (IRB) at The Children's Hospital of Philadelphia and NYU School of Medicine.

Mice.

Wild-type C57/B16 male mice, or SAP knockout mice (B6.129S6-Sh2d1a$^{tm1Pls}$/J; The Jackson Laboratory), at 6-12 weeks of age were used.

Statistics.

Values are reported as mean±SEM. Statistical analyses were performed using Student's t-test and ANOVA analysis. All statistical analyses were performed using GraphPad Prism (Ver. 6.0).

Additional Methods

General Reagents.

RPMI 1640 medium, Dulbecco's Modified Eagle's Medium (DMEM), Dulbecco's phosphate-buffered saline (DPBS) and fetal bovine serum (FBS) were purchased from Life Technologies. Opti-MEM-1 was purchased from Invitrogen. Ficoll-Paque was purchased from GE. BCA assay was purchased from Pierce Biotechnology. Poly-L-lysine, fibronection, and orthovanadate were purchased from Sigma. Pervanadate was prepared by mixing orthovanadate and $H_2O_2$ at 1:1 ratio and used at final concentration of 50 µM. SHP099 was purchased from Medchem Express (HY-100388A; MCE).

Cell Culture, Transfection, and Stimulation.

Primary human T cells were isolated from whole blood using RosetteSep (Stemcell) followed by Ficoll-Paque, according to the manufacturer's instructions. The cells were maintained in enriched media (HEPES 25 mM, Sodium pyruvate 100 mM, Nonessential amino acid, and L-Glutamine) at 5% C02 and 37° C. Jurkat T cells were obtained from the ATCC and maintained in RPMI medium supplemented with 10% FBS and 1% Pen/Strep. 293T cells were obtained from the ATCC and maintained in DMEM media supplemented with 10% FBS and 1% Pen/Strep. Constructs were introduced into the cells by nucleofection (Lonza) with an efficiency of 50 to 70%. Cells were stimulated at a 1:3 ratio with magnetic beads ($3 \times 10^6$ beads per well) conjugated with anti-CD3 (UCHT1; R&D) and IgG1 (R&D) or with anti-CD3 and PD-L2-IgG1 (R&D). Magnetic beads (Invitrogen) were coated with anti-CD3 (25%), PD-L2-Ig fusion protein (50%) and control IgG comprised the remaining of the total protein. For the proliferation assay, we used beads coated with anti-CD28 (eBioscience, 25%), anti-CD3 (25%) and PD-L1-IgG1 (R&D, 50%). Constructs were introduced into 293T cells using the SuperFect transfection reagent (Qiagen) according to the manufacturer's protocol.

Antibodies and Recombinant Proteins.

Antibodies for T cell activation were described above. The following antibodies were used for biochemical assays: Anti-SHP2 (SC-280; Santa Cruz), anti-phosphotyrosine (4G10; Millipore), anti-GFP-Agarose (D153; MBL), anti-GFP (118144600; Roche), anti-SAP (2778; Cell Signaling), anti-pErk (9106; Cell Signaling) and anti-pZap70 (2701; Cell Signaling), anti-actin (1616; Santa Cruz), and anti-pPLC gamma (2821; Cell Signaling). Recombinant human SAP (His tagged; 101112) and GST-tagged recombinant human SHP2 (catalytic domain; 42578) were purchased from Abcam. Recombinant pCD3 (GHDGLY(p)QGLST), pSLAMF5 (SKKTIY(p)TYIMA), pCD28 (LHSDY(p)MNMTP and HYQPY(p)APPRD) peptides were synthesized by GenScript.

DNA Constructs.

pMSCV-PD-1-YFP was a Gift from James Allison (MD Anderson).

Mutations in the ITIM and ITSM domains of the PD-1 tail (Y223F, Y248F, Y223E, Y248E) were generated using the QuikChange Site-Directed Mutagenesis Kit (Agilent) and the PD-1-tail-GST and PD-1-full length-GFP fusion constructs were generated from pGEX-2T and pGFP-N1 respectively, by PCR cloning. Residues 192-288 of PD-1 were used for cloning the tail of PD-1. pSAP-CHERRY and pSAP-GFP were generated by cloning the SH2D1A genes from pDORN201-SH2D1A (DNASU) into mCherry-hLC3B-pcDNA3.1 and pGFP-N1 (Invitrogen). mCherry-hLC3B-pcDNA3.1 was a gift from David Rubinsztein (Addgene #40827) (Traffic 2008; 9:574-87). WT SAP was generated from pLX304-SH2D1A (DNASU). pMD2G and psPAX2, the backbone plasmids for the lentiviral vectors that were used for stable transfection, were gifts from Mark R. Philips (NYU). pMSCV-SHP2-flag and pMSCV-null were previously described (Mohi M G, et al. (2005) *Cancer cell* 7(2):179-191).

Generating Stable Knockdown Jurkat T Cells.

SAP was stably knocked down in Jurkat T cells by RNA interference using Mission shRNA plasmids (Sigma). Lentiviral particles were generated by transfecting HEK293T-cells with pMD2G, psPAX2, and the shRNA plasmid using SuperFect (Qiagen). T cells were transduced by centrifugation and selected with puromycin.

siRNA for knockdown in primary human T-cells.

SMARTpool ON-TARGETplus SH2D1A (SAP), SHP2, and non-targeting control siRNA (Dharmacon) were used according to the manufacturer's instruction.

Cytokine Analysis.

To determine the concentration of secreted IL-2 and IFN-γ following stimulation, human or mouse IL-2 and IFN-γ ELISA kits (BioLegend) were used according to the manufacturer's protocols. Cells were stimulated with antibody coated beads as described in Cell culture, transfection, and stimulation section for 24-48 hours following supernatant collection and analysis.

Cell Proliferation Assay.

Cell proliferation assay was performed using tetrazolium compound based CellTiter 96® AQueous One Solution Cell Proliferation (MTS) assay (Promega). T cells were activated with antibody-coated beads and cultured for 4-6 days, with MTS cell viability assay performed daily or every other day according to the manufacturer's instructions.

Immunoprecipitation and Affinity Enrichment.

Cell lysates were mixed with anti-GFP monoclonal antibody coupled to agarose beads to enrich GFP tagged proteins according to the manufacturer's protocols. Pull down lysates were separated by tris-glycine PAGE and transferred to nitrocellulose filters and visualized as described (Azoulay-Alfaguter et al., *The Journal of allergy and clinical immunology* 135(2):564-567). Bacterial expression vectors were used to transform competent BL21 *E. coli* cells, which were grown on LB/ampicillin plates overnight. IPTG (isopropyl-1-thio-b-D-galactosidase) induction, recombinant protein immobilization on glutathione sepharose beads (Thermo Scientific), binding assays and analyses of bound proteins were conducted as described (Li et al., *The EMBO journal* 23(5):1112-1122). The GST-tagged baits were mixed with the pervanadate-treated cell lysate for 24 hours at 4 degrees, before subjecting the affinity purified proteins to analysis. SAP was precipitated using pull-down polyHis protein: protein interaction kit (Pierce).

Phosphatase Activity.

293T cells were transfected with pMSCV-SHP2, pMSCV empty vector, PD1-WT-GFP, PD1-Y223F-GFP or PD1-Y248F-GFP for 48 hours, followed by pervanadate treatment and immunoprecipitation using anti-GFP mAb-Agarose. The anti-GFP mAb-Agarose beads that were used for immunoprecipitation were then used for a pull-down of the SHP2/null transfected cells, and phosphatase activity on the beads was assessed using pNPP (Sigma). To determine kinetic parameters, a fixed amount of purified GST-WT SHP2 catalytic domain (0.2 ug) was incubated with variable concentrations of the following substrates: RRLIEDAE(p)YAARG (Upstate 12-217), GHDGLY(p)QGLST (GenScript), SKKTIY(p)TYIMA (GenScript), LHSDY(p)MNMTP (GenScript), and HYQPY(p)APPRD (GenScript) in PTP assay buffer (Phosphatase assay kit; Upstate 17-313) in total volume of 150 uL (20 mM Hepes, 150 mM NaCl, 2 mM $MgCl_2$, 1 mM TCEP, pH 7). Reactions were carried out for 5 minutes at 25° C. The reactions were quenched by addition of 0.5 M EDTA, pH 8. Phosphatase release was quantified by adding Malachite Green (Malachite Green phosphatase detection kit; R&D DY996) to the supernatants, and measuring absorbance at 620 nm after 15 minutes at room temperature and comparing values to a standard curve generated with varying amount of $KH_2PO_4$. All reactions fell within the linear range. Phosphatase activity is expressed in pmol Pi released/5 min/0.2 pmol enzyme). Each data point represents triplicates.

Flow Cytometry.

T cells were stained with fluorescently conjugated antibodies specific for PD-1 or CD69 in FACS Buffer, then washed and fixed in 1% paraformaldehyde. Events were recorded using FACSCalibur (BD), and analyzed using FlowJo software. For CD3ζpY142 flow cytometry, $5\times10^5$ human T cells were resuspended in cold PBS with 2% FBS and 1 ug/ml of each anti-human CD3 and anti-human CD28 (both from BioLegend, San Diego, US) with or without human PD-L1 tagged with mouse IgG Fc (Acro Biosystems, US). The cells were incubated on ice for 20 min, washed once with cold PBS with 2% FBS and resuspended in cold PBS with 2% FBS containing 1 ug/ml of goat anti-mouse Ig. Next, the cells were incubated on ice for another 20 min before transferring to a 37C water bath for 5 min. Following stimulation, the cells were re-suspended in Fixation Buffer (BioLegend), incubated for another 15 min at 37° C. and washed with cold PBS with 2% FBS. The TruePhos™ permeabilization buffer protocol for intracellular phospho protein analysis from BioLegend was followed according to the manufacturer's instructions to determine the levels of phosphorylated CD3ζTyr142. TruePhos™ permeabilized cells were stained with anti-human CD247 Tyr142 antibody (clone K25-407.6; BD Biosciences) and the samples were acquired on BD LSR flow cytometer. Flow cytometry data analyses were performed with FlowJo data analysis software (FlowJo®, LLC). For Intracellular SAP staining and surface PD-1 expression, CD3+ T cells were stained for 30 min at 4° C. with the following anti-human antibodies (all from BioLegend): APC/Cy7-CD3 (clone HIT3a), Alexa Fluor-CD4 (clone RPA-T4), Pacific Blue-CD8 (clone RPA-T8), Alexa Fluor 488-CCR7 (clone G043H7), Brilliant Violet 605-CD45RA (clone HI100) and Brilliant Violet 711-PD-1 (clone EH12.2H7). Next, the cells were washed twice with cold PBS containing 2% FBS and fixed in 2% paraformaldehyde. Fixed cells were washed twice with Intracellular Staining Permeabilization Wash Buffer (BioLegend) and stained with anti-human SAP (SH2D1A) antibody (clone XLP-1D12, eBioscience) for 30 min at room temperature. The cells were washed after intracellular staining and acquired on BD LSR flow cytometer.

Static Adhesion Assay.

Static T cell adhesion to fibronectin-coated plates was performed as reported (Strazza et al., *Journal of visualized experiments: JoVE* (88)).

XLP Patients and Healthy Controls.

The patients and healthy human controls provided informed consent for immunologic studies. The study was approved by the Institutional Review Board (IRB) at The Children's Hospital of Philadelphia and NYU School of Medicine.

Mice.

Animal studies were approved by the New York University institutional animal care and use committee. Wild-type C57/B16 male mice, or SAP knockout mice 10 (B6.129S6-Sh2d1a$^{tm1Pls}$/J; The Jackson Laboratory), at 6-12 weeks of age were used. Spleens were harvested and cells were collected through a 40-μm nylon cell strainer and washed in PBS containing 1% glucose, followed by lymphocyte isolation (Dynabeads Mouse CD3 Negative Selection, Invitrogen). Lymphocytes were treated with beads coated with the indicated ligands for 48 h or more. Cell titer 96 AQueous one solution cell proliferation assay (Promega) was used to monitor proliferation and mouse IL-2 ELISA MAX kit (Biolegend) was used to quantify IL-2 secretion.

Statistics.

Values are reported as mean±SEM. Statistical analyses were performed using Student's t-test and ANOVA analysis. All statistical analyses were performed using GraphPad Prism (Ver. 6.0).

Data Availability.

All relevant data are available within the manuscript or from the authors upon reasonable request.

Mass Spectrometry (LC-MS/MS).

The samples were digested in gel and analyzed on LCMS as in (Drummond et al., *Scientific reports* 5:15456). The MS/MS spectra were searched against the UniProt Human reference proteome database (downloaded 2-25-16) (UniProt C (2015) UniProt: a hub for protein information. *Nucleic acids research* 43(Database issue):D204-212), with wild type and phosphor impaired GST-PD1 sequences inserted into the database, using Sequest within Proteome Discoverer. Carbamidomethylation of cysteine was set as a fixed, oxidation of methionine and deamidation of asparagine and glutamine were set as variable modifications. The mass tolerance was set to 10 ppm for both MS1 and MS/MS searches. FDR filtration was done at 1% FDR using a standard target-decoy database approach. Proteins identified with less than two unique peptides were excluded from analysis. For analysis of phosphorylation of PD-1, the MS/MS spectra were searched against the UniProt Human reference proteome database with wild type and phosphor impaired GST-PD-1 sequences inserted into the database using Byonic (Protein Metrics).

The affinity purified samples were eluted off the beads by boiling with SDS loading buffer. The samples were reduced with 2 μl of 0.2M DTT for one hour or 1 hour and alkylated with 2 μl of 0.5M iodoacetamide at room temperature in the dark for 45 minutes. Following alkylation, samples were loaded onto a NuPAGE® 4-12% Bis-Tris Gel 1.0 mm (Life Technologies Corporation) and ran for 15 minutes at 200V. The gel was stained using GelCode Blue Stain Reagent (Thermo Scientific) following manufactures instruction. Each lane was cut into approximately 1 mm3 pieces. For each sample, the dominant GST-PD1 bait and other dominant bands were excised, prepped and analyzed on the LCMS separately from the rest of the sample to increase the dynamic range of experiment. Excised gel pieces were destained in 1:1 v/v solution of methanol and 100 mM ammonium bicarbonate at 4° C. with agitation. The destain solution was changed every 15 minutes at least 6 times until the gel pieces had no visibly blue stain left. Gel pieces were partially dehydrated with an acetonitrile rinse and further dried in a SpeedVac concentrator for 20 minutes. 200 ng of sequencing grade-modified trypsin (Promega) was added to the dried gel pieces. After trypsin was absorbed, 180p1 of 100 mM ammonium bicarbonate was added to cover the gel pieces and digestion proceeded overnight on a shaker at RT. Peptide extraction was performed, by adding 180p1 of R2 20 μm Poros bead slurry in 5% formic acid and 0.2% trifluoroacetic acid to each sample. Samples were incubated with agitation at 4° C. for 4 hours. The beads were loaded onto equilibrated C18 ziptips (Millipore) using a microcentrifuge for 30 sec at 3000 RPM. Gel pieces were rinsed three times with 0.1% TFA and each rinse was added to the corresponding ziptip followed by microcentrifugation. Extracted poros beads were further rinsed with 0.5% acetic acid. Peptides were eluted by addition of 40% acetonitrile in 0.5% acetic acid followed by the addition of 80% acetonitrile in 0.5% acetic acid. The organic solvent was removed using a SpeedVac concentrator and the samples were reconstituted in 0.5% acetic acid. An aliquot of each sample was loaded onto the EASY spray 50 cm C18 analytical HPLC column with <2 μm bead size using the auto sampler of an EASY-nLC 1000 HPLC (ThermoFisher) in solvent A (2% acetonitrile, 0.5% acetic acid). The peptides were gradient eluted directly into a QExactive mass spectrometer (Thermo Scientific) using a one hour gradient from 2% to 31% solvent B (90% acetonitrile, 0.5% acetic acid), followed by 10 minutes from 31% to 40% solvent B and 10 minutes from 40% to 100% solvent B. The mass spectrometer acquired high resolution full MS spectra with a resolution of 70,000, an AGC target of 1e6 with a maximum ion time of 120 ms, and scan range of 400 to 1500 m/z. Following each full MS twenty data-dependent high resolution HCD MS/MS spectra were acquired using a resolution of 17,500, AGC target of 5e4 with maximum ion time of 120 ms, one microscan, 2 m/z isolation window, fixed first mass of 150 m/z, and Normalized Collision Energy (NCE) of 27 and dynamic exclusion of 30 seconds. The MouseMine query (Motenko H, Neuhauser S B, O'Keefe M, & Richardson J E (2015) MouseMine: a new data warehouse for MGI. *Mammalian genome: official journal of the International Mammalian Genome Society* 26(7-8):325-330) was performed on the filtered data set as described. The input data for MouseMine query consisted of PSMs per protein-group, where each protein group was associated with the corresponding gene name as well as two columns of augmented information: The first column indicates whether the protein group contains at least one protein with an SH2 domain according to UniProt (2014). The second column identifies the protein group as containing a homolog of a gene known to exhibit an immune phenotype in mouse (Berger A H, et al. (2016) High-throughput Phenotyping of Lung Cancer Somatic Mutations. *Cancer cell* 30(2):214-228). The query for UniProt was: annotation: (type: "positional domain" sh2) AND organism: "*Homo sapiens* (Human) [9606]". For the MouseMine query, one of the example query templates with the gene specific filter was removed prior to querying. Any missing data was set to 0 PSMs. In addition, a column was defined representing the gene name(s) per protein group when possible but defaults to the protein name(s) when no gene name was provided. The data was then filtered to only include protein groups which: 1. had strictly no PSMs in the control sample, but contained PSMs in wild type (WT) and phospho-deficient samples; 2. were observed in at least three experiments; 3. had a total of at least nine PSMs. The ratios of PSM for WT versus phospho-deficient samples were calculated and a one-sided permutation-test was applied per row. No correction for multiple hypothesis testing was done for this data and even without a multiple-hypothesis correction only a single protein group could be considered significant. The results are then plotted in a one-sided volcano plot (FIG. 1*f*).

While the present invention has been described through specific embodiment, routine modifications to the disclosure will be apparent to those skilled in the art. Such modifications are intended to be within the scope of the disclosure.

What is claimed is:

1. A method of treating an individual afflicted with cancer comprising:
   in a sample of blood cells obtained from the individual determining a level of signaling lymphocyte activation molecule-associated protein (SAP) to be lower than a reference SAP level, wherein the reference SAP level is the level of SAP from an individual or individuals without cancer; and administering to the individual afflicted with cancer a therapy comprising PD-1 inhibition therapy, and further comprising administering to the individual a SHP2 inhibitor.

2. The method of claim 1, wherein the SHP2 inhibitor is TNO155, 1-4-6-bromonaphthalen-2-yl) thiazol-2-yl)-4-methylpiperidin-4-amine, NSC-117199, NSC-87877, SPI-112, SPI-112Me, Fumosorinone, demethylincisterol A$_3$, 11a-1, Cryptotanshinone, siRNA, shRNA, CRISPR/Cas9 or other gene expression disrupter of PTPN11.

3. The method of claim 1, wherein cancer is melanoma, lung cancer, kidney cancer, bladder cancer, head and neck cancer, Hodgkin's lymphoma, or urinary tract cancer.

4. The method of claim 1, wherein the PD-1 inhibition therapy comprises administration of one or more of the following: pembrolizumab, nivolumab, atezolizumab, avelumab, and durvalumab.

5. The method of claim 1, wherein the blood cells are peripheral blood cells or peripheral T cells.

* * * * *

UNITED STATES PATENT AND TRADEMARK OFFICE
CERTIFICATE OF CORRECTION

| | | |
|---|---|---|
| PATENT NO. | : 11,110,171 B2 | Page 1 of 1 |
| APPLICATION NO. | : 16/956451 | |
| DATED | : September 7, 2021 | |
| INVENTOR(S) | : Adam Mor and Ben Neel | |

It is certified that error appears in the above-identified patent and that said Letters Patent is hereby corrected as shown below:

In the Specification

Column 1, Lines 13-16 should read:
--This invention was made with government support under grant numbers R01 AI125640, CA049152, and CA016087 awarded by The National Institutes of Health. The government has certain rights in the invention.--

Signed and Sealed this
Sixth Day of December, 2022

Katherine Kelly Vidal
*Director of the United States Patent and Trademark Office*